United States Patent [19]

Morisawa et al.

[11] Patent Number: 4,898,862
[45] Date of Patent: Feb. 6, 1990

[54] 1,2,4-TRIAZINONE DERIVATIVES, THEIR PREPARATION AND USE

[75] Inventors: Yasuhiro Morisawa; Mitsuru Kataoka; Mitsuo Sugiyama; Fujio Saito; Hiroyuki Koike; Takeshi Oshima; Yasuo Simoji; Hitoshi Nagahori, all of Tokyo, Japan

[73] Assignee: Sankyo Company Limited, Tokyo, Japan

[21] Appl. No.: 26,290

[22] Filed: Mar. 16, 1987

[30] Foreign Application Priority Data

Mar. 20, 1986 [JP] Japan .................................. 61-62593
Apr. 2, 1986 [JP] Japan .................................. 61-75996
Apr. 14, 1986 [JP] Japan .................................. 61-85255

[51] Int. Cl.$^4$ ............... C07D 253/06; C07D 401/12; C07D 403/12; A61K 31/53
[52] U.S. Cl. ............................ 514/236.2; 544/242; 544/231.8; 544/232.2; 544/227.8; 544/182; 544/60; 544/112; 544/83; 544/58.6; 540/598; 540/575; 514/218; 514/212
[58] Field of Search .............. 544/182, 60, 112, 83, 544/58.6; 514/242, 231.8, 232.2, 236.2, 227.8, 218, 212; 540/598, 575

[56] References Cited

FOREIGN PATENT DOCUMENTS 052442 5/1982 European Pat. Off. .
086301 8/1983 European Pat. Off. .
122627 10/1984 European Pat. Off. .
123254 10/1984 European Pat. Off. .

Primary Examiner—John M. Ford
Attorney, Agent, or Firm—Frishauf, Holtz, Goodman & Woodward

[57] ABSTRACT

Compounds of formula (I):

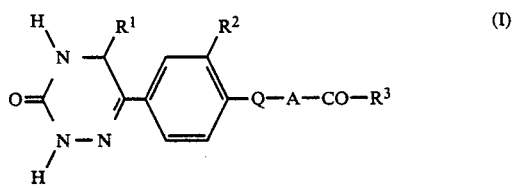

(in which: $R^1$ is hydrogen or alkl; $R^2$ is a variety of groups or atoms; $R^3$ is optionally substituted hydroxy or —(NH)$_n$—NR$^5$R$^6$, wherein $R^5$ and $R^6$ are a variety of groups or atoms, preferably alkyl substituted by heterocyclic, and n is 0 or 1; Q is oxygen or sulfur; and A is a $C_1$-$C_6$ alkylene group) have valuable cardiotionic activity and may be used for the treatment of cardiac disorders. They may be prepared from corresponding compounds containing a benzene ring with a group —QH at the 1-position and a group —CO—CHR$^1$—NH—COOR$^7$ at the 4-position by ring closure and introduction of the group of formula —A—CO—R$^3$ in any order.

23 Claims, No Drawings

1,2,4-TRIAZINONE DERIVATIVES, THEIR PREPARATION AND USE

BACKGROUND TO THE INVENTION

The present invention relates to a series of novel 6-(4-substituted phenyl)-1,2,4-triazin-3(2H)-one derivatives and provides processes for their preparation, methods of using them and compositions containing them. The compounds of the invention are characterized by having a 1,2,4-triazin-3(2H)-one group at the 1-position of the phenyl ring and a substituent on the 4-position of the phenyl group, which substituent is chosen from a limited class of substituted carbonylalkoxy or carbonylalkylthio groups.

The compounds of the invention have exhibited a variety of valuable therapeutic activities, including a cardiotonic activity (notably a stimulant activity arising from potentiation of the contractions of the heart), antihypertensive activity, the ability to inhibit gastric secretions and the ability to inhibit blood platelet aggregation; however, it is envisaged that the primary value of the compounds of the invention will arise as a result of their cardiotonic activity.

A variety of 6-(substituted phenyl)-3(2H)-1,2,4-triazinones is known, and some of these are thought to have useful cardiac activities. For example, certain such compounds are said in European Patent Publication No. 52 442 to have cardiotonic and vasodilator activities. Other, somewhat similar, compounds are disclosed in European Patent Publication No. 123 254 and are said to have anti-hypertensive activity, the ability to inhibit gastric secretions and the ability to inhibit blood platelet aggregation, whilst those disclosed in European Patent Publication No. 122 627 are said to be useful in the treatment of hypertension, thrombosis and ulcers in human beings and other animals. British patent specification No. 1 383 906 (equivalent to U.S. patent specifications No. 3 975 388 and No. 4 088 762) and Japanese Patent Application Kokai (i.e. as laid open to public inspection) No. 8015/83 also disclose compounds which are said to have anti-hypertensive activity, but these are pyridazinone derivatives, unlike the 1,2,4-triazin-3(2H)-one derivatives of the present invention.

The compounds of European Patent Publication No. 123 254 are triazinone derivatives and the compounds of European Patent Publication No. 52 442 include some triazinone derivatives. However, the triazinone derivatives of this prior art differ from the compounds of the present invention in that the compounds of the invention all contain certain specified substituted carbonylalkoxy or carbonylalkylthio substituents on the 4-position of the phenyl group, and we have surprisingly found that compounds containing such a substituent possess significantly better cardiotonic activity than do the prior art compounds.

BRIEF SUMMARY OF INVENTION

It is, therefore, an object of the present invention to provide a series of 1,2,4-triazinone derivatives possessing valuable cardiotonic activity.

It is a further object of the invention to provide a composition containing such compounds.

It is a still further object of the invention to provide for the use of such compounds to treat a variety of ailments, including cardiac insufficiency.

The compounds of the invention may be represented by the formula (I):

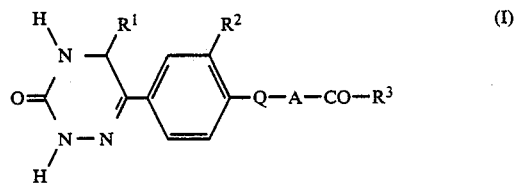

wherein:

$R^1$ represents a hydrogen atom or a $C_1$–$C_6$ alkyl group;

$R^2$ represents a hydrogen atom, a halogen atom, a $C_1$–$C_6$ alkyl group, a $C_1$–$C_6$ alkyl group having at least one halogen substituent, a nitro group, an amino group, a protected amino group, an alkylamino group in which the alkyl part is $C_1$–$C_6$, a dialkylamino group in which each alkyl part is $C_1$–$C_6$, a cyano group, a carbamoyl group, an alkylcarbamoyl group in which the alkyl part is $C_1$–$C_6$, a dialkylcarbamoyl group in which each alkyl part is $C_1$–$C_6$, a ureido group, an alkylureido group in which the alkyl part is $C_1$–$C_6$, a dialkylureido group in which each alkyl part is $C_1$–$C_6$, a carboxy group or a protected carboxy group;

Q represents an oxygen atom or a sulfur atom;

A represents a $C_1$–$C_6$ alkylene group;

$R^3$ represents a hydroxy group, a $C_1$–$C_6$ alkoxy group, an aryloxy group, an aralkyloxy group in which the alkyl part has from 1 to 6 carbon atoms or a group of formula —$(NH)_n$—$NR^5R^6$, wherein n is 0 or 1; and $R^5$ and $R^6$ are independently selected from the group consisting of hydrogen atoms, $C_1$–$C_{10}$ alkyl groups, substituted $C_1$–$C_{10}$ alkyl groups having at least one substituent selected from the group consisting of substituents (a), $C_2$–$C_6$ alkenyl groups, $C_3$–$C_7$ cycloalkyl groups, aryl groups and heterocyclic groups, or $R^5$ and $R^6$, together with the nitrogen atom to which they are attached, form a heterocyclic group;

said aryl groups and aryl parts of groups containing an aryl group are $C_6$–$C_{14}$ carbocyclic aryl groups which are unsubstituted or have at least one substituent selected from the group consisting of substituents (b);

said heterocyclic groups and heterocyclic parts of groups containing a heterocyclic group contain from 5 to 14 ring atoms, of which from 1 to 5 are hetero-atoms selected from the group consisting of nitrogen, oxygen and sulfur hetero-atoms, said heterocyclic groups being unsubstituted or having at least one substituent selected from the group consisting of said substituents (b) and oxygen atoms;

substituents (a):

halogen atoms, hydroxy groups, $C_1$–$C_6$ alkoxy groups, aryloxy groups, aralkyloxy groups in which the alkyl part has from 1 to 6 carbon atoms, carboxy groups, protected carboxy groups, carbamoyl groups, alkylcarbamoyl groups in which the alkyl part is $C_1$–$C_6$ and is unsubstituted or has at least one substituent selected from the group consisting of substituents (a) but excluding said alkylcarbamoyl groups, dialkylcarbamoyl groups in which each alkyl part is $C_1$–$C_6$, $C_3$–$C_7$ cycloalkyl groups, aryl groups, heterocyclic groups, amino groups, protected amino groups and amino groups having one or two substituents selected from the group consisting of $C_1$–$C_6$ alkyl groups, aryl groups, and heterocyclic groups; and substituents (b):

the atoms and groups defined above as substituents (a), $C_1$–$C_6$ alkyl groups, $C_1$–$C_6$ alkyl groups having at least one substituent selected from the group consisting of substituents (a), aliphatic carboxylic acyl groups, substituted $C_2$–$C_6$ aliphatic carboxylic acyl groups having at least one substituent selected from the group consisting of substituents (a), aromatic carboxylic acyl groups, aralkylcarbonyl groups, heterocyclic carbonyl groups, $C_2$–$C_7$ alkoxycarbonyl groups, aralkyloxycarbonyl groups; $C_1$–$C_6$ alkylsulfonyl groups, arylsulfonyl groups, sulfamoyl groups and $C_1$–$C_6$ alkylsulfamoyl groups; and pharmaceutically acceptable acid addition salts thereof PROVIDED THAT: when $R^2$ represents said hydrogen atom or said nitro, amino or cyano group, THEN $R^3$ represents a group of formula —(NH-)$_n$—NHR$^6$, where n is 0 or 1 and $R^6$ represents said $C_1$–$C_6$ alkyl group having at least one heterocyclic substituent.

The invention also provides methods of preparing the compounds of the invention, which are described in more detail hereafter.

The invention also provides a pharmaceutical composition for the treatment of cardiac disorders, comprising a cardiotonic agent in admixture with a pharmaceutically acceptable carrier, diluent or excipient, wherein said cardiotonic agent is selected from the group consisting of compounds of formula (I) and pharmaceutically acceptable acid addition salts thereof.

The invention still further provides a method of treating cardiac disorders in an animal, e.g. a mammal (including humans), by administering to said animal an active compound selected from the group consisting of compounds of formula (I) and pharmaceutically acceptable acid addition salts thereof.

DETAILED DESCRIPTION OF INVENTION

In the compounds of the invention, where $R^1$, $R^2$ or various substituents, as defined above, are $C_1$–$C_6$ alkyl groups, these groups may be straight or branched chain groups and examples include the methyl, ethyl, propyl, isopropyl, butyl, isobutyl, sec-butyl, t-butyl, pentyl, isopentyl, 2methylbutyl, neopentyl, t-pentyl, hexyl, 4-methylpentyl, 3-methylpentyl, 2-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl and isohexyl groups, of which the $C_1$–$C_4$ alkyl groups, particularly the methyl, ethyl, propyl, isopropyl, butyl, isobutyl and sec-butyl groups, are preferred, the methyl and ethyl groups being more preferred.

Where $R^5$ or $R^6$ represents a $C_1$–$C_{10}$ alkyl group, this likewise may be a straight or branched chain group and examples include the methyl, ethyl, propyl, isopropyl, butyl, isobutyl, sec-butyl, t-butyl, pentyl, isopentyl, 2-methylbutyl, neopentyl, t-pentyl, hexyl, 4-methylpentyl, 3-methylpentyl, 2-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, isohexyl, heptyl, 1-methylhexyl, 2-methylhexyl, 1-ethylpentyl, octyl, 3-methylheptyl, 4-methylheptyl, 2-ethylhexyl, nonyl, 1-methyloctyl, 2-methyloctyl, 3-ethylheptyl, decyl, 4-methylnonyl, 5-methylnonyl and 6-ethyloctyl groups. Where the alkyl group represented by $R^5$ or $R^6$ is unsubstituted, we prefer the groups selected from those defined above which have from 1 to 6 carbon atoms. On the other hand, where the group represented by $R^5$ or $R^6$ is substituted, we prefer that the groups should be chosen from those having from 1 to 6 carbon atoms, more preferably from 2 to 4 carbon atoms.

Where $R^2$, substituent (a) or substituent (b) represents a halogen atom, this is preferably a fluorine, chlorine, bromine or iodine atom.

Where $R^2$ represents a $C_1$–$C_6$ alkyl group having at least one halogen substituent, the halogen substituent is preferably selected from the group consisting of fluorine, chlorine, bromine and iodine atoms, more preferably fluorine and chlorine atoms. The alkyl group itself may be a straight or branched chain alkyl group and examples of such groups are given above in relation to the groups which may be represented by, inter alia, $R^1$ and $R^2$; the alkyl group is more preferably a $C_1$–$C_4$ alkyl group, for example a methyl, ethyl, propyl, isopropyl or butyl group, and most preferably a methyl group. The number of halogen substituents is limited only by the number of carbon atoms available to substitute, and the substituted alkyl group could be anything from a monohaloalkyl group to a perhaloalkyl group. In general, the most commonly available haloalkyl groups contain 1, 2 or 3 halogen atoms and, for this reason alone, such mono-, di- and tri-haloalkyl groups are preferred, but it should be borne in mind that any greater number of halogen atoms up to complete halogenation is possible. Examples of preferred haloalkyl groups include the fluoromethyl, chloromethyl, trifluoromethyl, 2-chloroethyl, 2,2,2-trichloroethyl, 3-fluoropropyl and 4-fluorobutyl groups, more preferably the trifluoromethyl group.

Where $R^2$ or substituent (a) or (b) represents a protected amino group, the protecting group may be selected from any such group known for use in organic chemistry, normally without restriction. The only restriction that may apply is where the compound of the invention is intended for pharmaceutical use, in which case it is necessary that the resulting compound should be pharmaceutically acceptable. Examples of suitable protecting groups include the aliphatic acyl groups, substituted aliphatic acyl groups, optionally substituted aromatic acyl groups and aralkyl groups.

Specifically, aliphatic acyl groups are aliphatic carboxylic acyl groups, which may be saturated or unsaturated, having from 1 to 7 carbon atoms (except for the unsaturated aliphatic acyl groups, which necessarily have at least 3 carbon atoms), preferably alkanoyl, alkenoyl, alkynoyl, alkoxycarbonyl (preferably $C_2$–$C_5$, i.e., the alkoxy part itself is $C_1$–$C_4$) and alkenyloxycarbonyl (preferably $C_3$–$C_5$ groups. Substituents on the substituted aliphatic acyl groups may be any of those defined generally as substituents (a) and exemplified herein. Examples of such alkanoyl groups include the formyl, acetyl, chloroacetyl, dichloroacetyl, trichloroacetyl, trifluoroacetyl, methoxyacetyl, ethoxyacetyl, propionyl, butyryl, isobutyryl, 4-halobutyryl (e.g. 4-chlorobutyryl and 4-bromobutyryl groups), valeryl, isovaleryl, pivaloyl, hexanoyl, isohexanoyl and heptanoyl groups. The $C_1$–$C_5$ saturated aliphatic acyl groups are preferred (particularly the formyl, acetyl, propionyl, butyryl, valeryl and isovaleryl groups), the acetyl group being the most preferred. In the case of the unsaturated aliphatic acyl groups, these necessarily have a minimum of 3 carbon atoms and so those employed in the present invention have from 3 to 7 carbon atoms, preferably from 3 to 5 carbon atoms. Examples of alkenoyl and alkynoyl groups include the acryloyl, methacryloyl, crotonoyl, isocrotonoyl, 3-butenoyl, (E)-2-methyl-2-butenoyl and propioloyl groups. Examples of the lower alkoxycarbonyl groups include the methoxycarbonyl, ethoxycarbonyl, t-butoxycarbonyl, 2,2,2-trichloroethoycarbonyl and isobutoxycarbonyl groups. Examples of the lower alkenyloxycarbonyl groups include the vinyloxycarbonyl and allyloxycarbonyl groups.

In the case of the aromatic acyl groups, the aromatic part is preferably as defined hereafter in relation to aryl groups (more preferably a phenyl or naphthyl group which may be substituted or unsubstituted) and examples include arylcarbonyl groups and aralkyloxycarbonyl groups. The aryl parts of said arylcarbonyl and aralkyloxycarbonyl groups may be unsubstituted or have at least one substituent selected from the group consisting of substituents (b), as defined above, preferably halogen atoms, sulfamoyl groups, $C_1$-$C_4$ alkylsulfamoyl groups, hydroxy groups, $C_1$-$C_4$ alkyl groups, haloalkyl groups (especially the trifluoromethyl group) and $C_1$-$C_4$ alkoxy groups. Specific examples of such aromatic acyl groups include the benzoyl, 2,4,6-trimethylbenzoyl, p-toluoyl, p-anisoyl, p-chlorobenzoyl, p-trifluorobenzoyl, p-methoxybenzoyl, benzyloxycarbonyl and p-bromobenzyloxycarbonyl groups.

The aralkyl groups used as protecting groups may be groups where the aryl part is as defined above and the alkyl part is a $C_1$-$C_6$ group; the same definition applies herein in relation to aralkyl groups generally. They are preferably such groups where the alkyl part is $C_1$-$C_3$, more preferably methyl, and the or each aryl part is as defined above and may be substituted or unsubstituted. Specific examples include the benzyl, p-nitrobenzyl, o-nitrobenzyl, triphenylmethyl, diphenylmethyl, bis(o-nitrophenyl)methyl, 9-anthrylmethyl, 2,4,6-trimethylbenzyl, p-bromobenzyl and p-methoxybenzyl groups.

Where $R^2$ or substituent (a) or (b) represents a mono- or di- alkylamino group, he or each alkyl part may be as exemplified above in relation to the groups which may be represented by $R^1$, more preferably the $C_1$-$C_4$ groups. Specific examples include the methylamino, ethylamino, propylamino, isopropylamino, butylamino, isobutylamino, sec-butylamino, t-butylamino, pentylamino, t-pentylamino, dimethylamino, diethylamino, dipropylamino, dibutylamino, methylethylamino and methylpropylamino groups.

Where $R^2$ or substituent (a) or (b) represents a mono- or di- alkylcarbamoyl group, the or each alkyl part may be as exemplified above in relation to the groups which may be represented by $R^1$, more preferably the $C_1$-$C_4$ groups. Specific examples include the methylcarbamoyl, ethylcarbamoyl, propylcarbamoyl, isopropylcarbamoyl, butylcarbamoyl, isobutylcarbamoyl, sec-butylcarbamoyl, t-butylcarbamoyl, pentylcarbamoyl, t-pentylcarbamoyl, dimethylcarbamoyl, diethylcarbamoyl, dipropylcarbamoyl, dibutylcarbamoyl, methylethylcarbamoyl and methylpropylcarbamoyl groups.

Where $R^2$ represents a mono- or di-alkylureido group, the or each alkyl part may be as exemplified above in relation to the groups which may be represented by $R^1$, more preferably the $C_1$-$C_4$ groups. Specific examples include the methylureido, ethylureido, propylureido, isopropylureido, butylureido, isobutylureido, sec-butylureido, t-butylureido, pentylureido, t-pentylureido, dimethylureido, diethylureido, dipropylureido, dibutylureido, methylethylureido and methylpropylureido groups.

Where $R^2$ or substituent (a) or (b) represents a protected carboxy group, the protecting group may be selected from any such group known for use in organic chemistry, normally without restriction. The only restriction that may apply is where the compound of the invention is intended for pharmaceutical use, in which case it is necessary that the resulting compound should be pharmaceutically acceptable. Examples of suitable protecting groups include: the $C_1$-$C_6$ alkyl groups defined above; aralkyl groups, such as the benzyl, p-nitrobenzyl, o-nitrobenzyl, triphenylmethyl, diphenylmethyl, bis(o-nitrophenyl)methyl, 9-anthrylmethyl, 2,4,6-trimethylbenzyl, p-bromobenzyl, p-methoxybenzyl and piperonyl groups; aliphatic acyloxymethyl groups, such as the acetoxymethyl, propionyloxymethyl, butyryloxymethyl, isobutyryloxymethyl and pivaloyloxymethyl groups; 1-(alkoxycarbonyloxy)ethyl groups, in which the alkoxy part is $C_1$-$C_6$, preferably $C_1$-$C_4$, such as the 1-methoxycarbonyloxyethyl, 1-ethoxycarbonyloxyethyl, 1-propoxycarbonyloxyethyl, 1-isopropoxycarbonyloxyethyl, 1-butoxycarbonyloxyethyl and 1-isobutoxycarbonyloxyethyl groups; carboxy-protecting groups capable of being hydrolyzed in vivo, such as the phthalidyl, (2-oxo-5-methyl-1,3-dioxolen-4-yl)methyl groups and (2-oxo-5-phenyl-1,3-dioxolen-4-yl)methyl groups; alkoxymethyl groups, in which the alkoxy part is $C_1$-$C_6$, preferably $C_1$-$C_4$, such as the methoxymethyl, ethoxymethyl, propoxymethyl, isopropoxymethyl, butoxymethyl and methoxyethoxymethyl groups; and halogenated $C_1$-$C_6$, preferably $C_1$-$C_4$, alkyl groups, such as the 2,2,2-trichloroethyl, 2-haloethyl (e.g. 2-chloroethyl, 2-fluoroethyl, 2-bromoethyl or 2-iodoethyl) and 2,2-dibromoethyl groups. Of these, the alkyl groups, the aralkyl groups, the aryl groups and carboxy-protecting groups capable of being hydrolyzed in vivo are preferred.

A represents a $C_1$-$C_6$ alkylene group, i.e. a bivalent saturated aliphatic hydrocarbon group attached by one of its valences to the atom represented by "Q" and by the other of its valences to the group —$COR^3$. The free valences may be on different carbon atoms or they may be on the same carbon atom, in which case such a group is sometimes referred to as an "alkylidene" group. The alkylene group may be a straight or branched chain group. Examples of such alkylene groups include the methylene, ethylidene, ethylene, propylene, trimethylene, propylidene, tetramethylene, 1-methyltrimethylene, 2-methyltrimethylene, 3-methyltrimethylene, pentamethylene and hexamethylene groups, of which $C_1$-$C_4$ alkylene groups, such as the methylene, ethylene, trimethylene and tetramethylene groups are preferred.

Where $R^3$ or substituent (a) or (b) represents a $C_1$-$C_6$ alkoxy group, this group may be a straight or branched chain group and examples include the methoxy, ethoxy, propoxy, isopropoxy, butoxy, isobutoxy, sec-butoxy, t-butoxy, pentyloxy, isopentyloxy, 2-methylbutoxy and hexyloxy groups, of which the $C_1$-$C_4$ alkoxy groups, particularly the methoxy, ethoxy, propoxy, isopropoxy, butoxy, isobutoxy and sec-butoxy groups, are preferred, the methoxy and ethoxy groups being more preferred.

Where $R^3$ or substituent (a) or (b) represents an aryloxy group, $R^5$ and/or $R^6$ or substituent (a) or (b) represents an aryl group or substituent (b) represents an aromatic acyl group or an arylsulfonyl group, the aryl group is a carbocyclic aryl group having from 6 to 14, preferably from 6 to 10, ring carbon atoms. The aryl group may be a monocyclic or fused polycyclic (preferably bicyclic) group and is more preferably the phenyl, 1-naphthyl or 2-naphthyl group. Such groups may be unsubstituted or substituted. Where the group is substituted, the minimum number of substituents is, of course, 1 and the maximum number is dictated by the number of carbon atoms capable of substitution and the nature of the substituents, which may impose steric constraints, as described in more detail hereafter in relation to substituents generally. The nature of the possible substituents is defined more generally above, but preferred substituents are $C_1$–$C_6$ (preferably $C_1$–$C_4$) alkyl groups, substituted $C_1$–$C_6$ (preferably $C_1$–$C_4$) alkyl groups (more preferably halogen-substituted alkyl groups), $C_1$–$C_6$ (preferably $C_1$–$C_4$) alkoxy groups, hydroxy groups, halogen atoms, sulfamoyl groups and $C_1$–$C_4$ alkylsulfamoyl groups. Examples of alkyl, substituted alkyl and alkoxy groups are as given above. Examples of halogen atoms include the fluorine, chlorine, bromine and iodine atoms. Particularly preferred substituents are the methyl, ethyl, methoxy, trifluoromethyl and sulfamoyl groups and the fluorine and chlorine atoms. Preferred aryl and aryloxy groups are the substituted and unsubstituted phenyl and phenoxy groups and, in this case, the more preferred substituents are the $C_1$–$C_4$ alkyl groups, the trifluoromethyl group, the $C_1$–$C_4$ alkoxy groups and halogen atoms, and the most preferred substituents are the methyl, ethyl, trifluoromethyl and methoxy groups and the fluorine and chlorine atoms.

Where $R^3$ or substituent (a) or (b) represents an aralkyloxy group, the aryl part may be any one of the aryl groups exemplified in the preceding paragraph and the alkyl part is a $C_1$–$C_6$ alkyl group (examples of which are given above), more preferably a $C_1$–$C_3$ alkyl group (e.g. a methyl, ethyl or propyl group) and most preferably a methyl or ethyl group. As with the aryl groups defined above, the aryl part of the aralkyloxy group may be substituted or unsubstituted, and examples of preferred aralkyloxy groups include the benzyloxy, p-methylbenzyloxy, p-bromobenzyloxy, m-chlorobenzyloxy, p-methoxybenzyloxy and phenethyloxy groups.

Where $R^5$ or $R^6$ represents an alkenyl group, this is a straight or branched chain group having from 2 to 6 carbon atoms, more preferably 3 or 4 carbon atoms. Examples of such groups include the vinyl, allyl, 1-propenyl, isopropenyl, methallyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl and 5-hexenyl groups, as well as the branched chain homologs of these groups. Of these, the allyl and methallyl groups are particularly preferred.

Where $R^5$, $R^6$, substituent (a) or substituent (b) represents a cycloalkyl group, this has from 3 to 7 ring carbon atoms and examples include the cyclopropyl, cyclobutyl, cyclopentyl, cyclohexyl and cycloheptyl groups. Of these, the cycloalkyl groups having 5 or 6 carbon atoms are preferred.

Where $R^5$, $R^6$, substituent (a), substituent (b) or $R^5$ and $R^6$ together with the nitrogen atom to which they are attached represents a heterocyclic group, this is a group containing from 5 to 14 ring atoms, of which from 1 to 5 are selected from the group consisting of nitrogen, oxygen and sulfur hetero-atoms. The heterocyclic group more preferably has from 5 to 8 ring atoms, of which from 1 to 3 are said hetero-atoms. In particular, we prefer that the heterocyclic group should contain from 5 to 7 ring atoms, most preferably 5 or 6 ring atoms, of which 1 or 2 are said hetero-atoms. The heterocyclic group may be aromatic in character or it may be non-aromatic and, if non-aromatic, its ring atoms may be fully saturated or it may include some unsaturated ring atoms.

Examples of such non-aromatic heterocyclic groups include the tetrahydrofuryl, tetrahydropyranyl, tetrahydrothienyl, tetrahydrothiopyranyl, aziridinyl, azetidinyl, pyrrolidinyl, piperidyl, hexahydroazepinyl, imidazolidinyl, oxazolidinyl, thiazolidinyl, morpholinyl (including morpholino). thiomorpholinyl (including thiomorpholino), piperazinyl and homopiperazinyl (=perhydro-1,4-diazepinyl) groups, any of which may be unsubstituted or substituted as defined above. As described more fully hereafter, there is no criticality as to the number of substituents on such substituted heterocyclic groups and examples of such substituents are as given herein. In the case of the non-aromatic heterocyclic groups, the preferred substituents are: aryl groups; substituted aryl groups (wherein the substituents are preferably at least the group or atom selected from the group consisting of halogen atoms. $C_1$–$C_4$ alkyl groups, $C_1$–$C_4$ alkoxy groups and trifluoromethyl groups); $C_1$–$C_4$ alkyl groups (especially the methyl or ethyl groups); substituted $C_1$–$C_4$ alkyl groups, wherein the substituents are at least one substituent selected from the group consisting of hydroxy groups, phenyl groups and substituted phenyl groups having at least one substituent selected from the group consisting of halogen atoms, $C_1$–$C_4$ alkyl groups, $C_1$–$C_4$ alkoxy groups and trifluoromethyl groups (especially the 2-hydroxyethyl group); $C_1$–$C_7$ alkanoyl groups and substituted $C_2$–$C_7$ alkanoyl groups (having at least one substituent selected from the group consisting of heterocyclic groups, $C_3$–$C_7$ cycloalkyl groups, halogen atoms, $C_1$–$C_4$ alkoxy groups and phenyl groups), e.g. as exemplified above; $C_2$–$C_5$ alkoxycarbonyl groups, e.g. as exemplified above; aralkyloxycarbonyl groups (wherein the alkyl part is $C_1$–$C_4$ alkyl and the aryl part is $C_6$–$C_{10}$ aryl or $C_6$–$C_{10}$ aryl having at least one substituent selected from the group consisting of halogen, $C_1$–$C_4$ alkyl, $C_1$–$C_4$ alkoxy and trifluoromethyl substituents), e.g. as exemplified above; aromatic carboxylic acyl groups, e.g. as exemplified above [especially the benzoyl groups and substituted benzoyl groups (having at least one substituent selected from the group consisting of halogen atoms, sulfamoyl groups, $C_1$–$C_4$ alkyl groups and $C_1$–$C_4$ alkoxy groups)]; heterocyclic acyl groups, e.g. as exemplified hereafter; $C_1$–$C_4$ alkylsulfonyl groups (especially the methanesulfonyl group); arylsulfonyl groups, wherein the aryl part is $C_6$–$C_{10}$ aryl or $C_6$–$C_{10}$ aryl having at least one substituent selected from the group consisting of halogen atoms, $C_1$–$C_4$ alkyl groups, $C_1$–$C_4$ alkoxy groups and trifluoromethyl groups (especially the benzenesulfonyl and p-toluenesulfonyl groups); the carbamoyl group; mono- and di-alkylcarbamoyl groups wherein the alkyl part is $C_1$–$C_4$ alkyl; heterocyclic groups, e.g. as exemplified hereafter; and oxygen atoms.

Where an oxygen atom is a substituent on a heterocyclic group, it may be attached to a ring carbon atom by covalent bonds, in which case it constitutes an "oxo" group (=O) or it may be attached by a coordinate bond to, for example, a nitrogen or sulfur atom (i.e. $>N\rightarrow O$ or $>S\rightarrow O$); of course, one or two oxygen atoms may be attached in this way to a ring sulfur atom, thus forming an N-oxide, S-oxide or S,S-dioxide, respectively.

In the case of the non-aromatic heterocyclic groups, these preferably have 5 or 7 ring atoms, of which from 1 to 3 are hetero-atoms selected from the group consisting of nitrogen, oxygen and sulfur atoms. Such groups may be unsubstituted or may have one or more of the substituents defined above.

Preferred examples of substituent on non-aromatic heterocyclic groups include the methyl, ethyl, phenyl, methoxycarbonyl, ethoxycarbonyl, benzyl, oxygen, hydroxyethyl, chlorophenyl, methoxyphenyl, trifluoromethylphenyl, pyridyl, benzhydryl, chlorobenzhydryl, difluorobenzhydryl, formyl, acetyl, valeryl, 3-butenoyl, chlorobutyryl, ethoxyacetyl, benzyloxycarbonyl, methanesulfonyl, toluenesulfonyl, benzoyl, chlorobenzoyl, methoxybenzoyl, nicotinoyl, isonicotinoyl, thenoyl, furoyl, methylcarbamoyl, p-chloro-m-sulfamoylbenzoyl, propionyl, isobutyryl, octanoyl, phenylpropionyl, cyclohexylpropionyl, heptanoyl and dimethoxybenzoyl groups.

In particular, we prefer, as substituted non-aromatic heterocyclic groups, the N-substituted piperazinyl groups and the optionally N-substituted 2,5-dimethylpiperazinyl and 2,6-dimethylpiperazinyl groups, wherein the N-substituents are selected from those defined above.

In the case of the aromatic heterocyclic groups, these preferably have 5 or 6 ring atoms, of which 1 or 2 are hetero-atoms selected from the group consisting of nitrogen, oxygen and sulfur atoms. Such groups may be unsubstituted or may have one or more of the substituents defined above; in the case of the aromatic heterocyclic groups, the preferred substituents are $C_1$-$C_4$ alkyl groups, particularly the methyl or ethyl groups. Examples of such substituted and unsubstituted aromatic heterocyclic groups include the furyl, thienyl, pyrrolyl, 1-methylpyrrolyl, 2,5-dialkylpyrrolyl (especially 2,5-dimethylpyrrolyl), pyridyl, 2-methylpyridyl, 3-ethylpyridyl, oxazolyl, thiazolyl, 4-methylthiazolyl and pyrimidinyl groups, of which the 2,5-dimethylpyrrolyl, thiazolyl and pyridyl groups are preferred.

Where $R^5$ and $R^6$, together with the nitrogen atom to which they are attached, represent a heterocyclic group, it may be chosen from any of those exemplified above, but, of course, in that case it necessarily has at least one nitrogen hetero-atom, through which it is attached to the remainder of the molecule. Such a group is preferably chosen from the non-aromatic heterocyclic groups.

Where substituent (b) represents a heterocyclic carbonyl group, the heterocyclic part may be chosen from any of those substituted and unsubstituted, aromatic and non-aromatic heterocyclic groups exemplified above. The aromatic heterocyclic groups, and particularly 5 and 6 membered heterocyclic groups containing 1 or 2 ring hetero-atoms selected from the group consisting of nitrogen, oxygen and sulfur atoms, are preferred. The most preferred heterocyclic carbonyl groups are the furoyl (e.g. 2-furoyl), pyridinecarbonyl (e.g., nicotinoyl, isonicotinoyl and picolinoyl) and thenoyl (e.g. 2-thenoyl) groups.

Where substituent (a) or substituent (b) is a mono-or di-substituted amino group, the substituent or substituents are chosen from the group consisting of $C_1$-$C_6$ alkyl groups, aryl groups (both of which are as exemplified above) and heterocyclic groups, as defined in more detail above in relation to heterocyclic groups generally. In the case of the di-substituted groups, the substituents may be the same or different.

Where substituent (b) represents an aliphatic carboxylic acyl group, a substituted $C_2$-$C_6$ aliphatic carboxylic acyl group, an aromatic carboxylic acyl group or a $C_2$-$C_7$ alkoxycarbonyl group, these may be chosen from any of those exemplified above in relation to amino protecting groups.

Where substituent (b) represents an aralkylcarbonyl group, its aralkyl moiety may be chosen from any of those exemplified above in relation to amino protecting groups.

In the case of the above groups which are defined as "substituted", the number of such substituents is not critical to the present invention, but will, instead, be determined by the number of positions available for substitution and possibly also by steric constraints. For example, where the substituents are relatively small groups or atoms, the only restriction may be the number of positions available for substitution and it may be possible for all such positions to be substituted. On the other hand, if one or more of the substituents are relatively "bulky" groups, steric considerations apply and the number of such substituents may thereby be limited. However, this is well known to those skilled in the art and requires no further definition here.

Preferred compounds of the present invention are those in which:

$R^1$ represents a hydrogen atom or a $C_1$-$C_6$ alkyl group;

$R_2$ represents a halogen atom, a $C_1$-$C_6$ alkyl group, a nitro group or a cyano group;

Q represents an oxygen atom or a sulfur atom;

A represents a $C_1$-$C_6$ alkylene group;

$R^3$ represents a group of formula $-(NH)_n-NR^5R^6$, wherein n is 0 or 1; and $R^5$ and $R^6$ are independently selected from the group consisting of hydrogen atoms, $C_1$-$C_{10}$ alkyl groups, substituted $C_1$-$C_{10}$ alkyl groups having at least one substituent selected from the group consisting of substituents (a'), $C_2$-$C_6$ alkenyl groups, aryl groups and $C_3$-$C_7$ cycloalkyl groups; and substituents (a'):

halogen atoms, $C_1$-$C_6$ alkoxy groups, aryloxy groups, aralkyloxy groups in which the alkyl part has from 1 to 6 carbon atoms, $C_3$-$C_7$ cycloalkyl groups, aryl groups, heterocyclic groups, amino groups, protected amino groups and amino groups having one or two substituents selected from the group consisting of $C_1$-$C_6$ alkyl groups;

and pharmaceutically acceptable acid addition salts thereof

PROVIDED THAT: when $R^2$ represents said nitro or cyano group, THEN $R^3$ represents a group of formula $-(NH)_n-NHR^6$, where n is 0 or 1 and $R^6$ represents said $C_1$-$C_6$ alkyl group having at least one heterocyclic substituent.

More preferred compounds of the present invention are those in which:

$R^1$ represents a hydrogen atom or a $C_1$-$C_4$ alkyl group;

$R^2$ represents a halogen atom or a $C_1$-$C_6$ alkyl group;

Q represents an oxygen atom or a sulfur atom;

A represents a $C_1$-$C_4$ alkylene group;

$R^3$ represents a group of formula $-(NH)_n-NR^5R^6$, wherein n is 0 or 1; and $R^5$ and $R^6$ are independently selected from the group consisting of hydrogen atoms, $C_1$-$C_6$ alkyl groups, $C_2$-$C_6$ alkenyl groups and substituted $C_2$-$C_4$ alkyl groups having at least one substituent selected from the group consisting of substituents (a''); and substituents (a''):

$C_1$–$C_6$ alkoxy groups, $C_3$–$C_7$ cycloalkyl groups, aryl groups and heterocyclic groups;
and pharmaceutically acceptable acid addition salts thereof.

The most preferred compounds of the present invention are those in which:

$R^1$ represents a hydrogen atom or a methyl group;
$R^2$ represents a halogen atom or a methyl group;
Q represents an oxygen atom;
A represents a $C_1$–$C_4$ alkylene group;
$R^3$ represents a group of formula —$NHR^6$, wherein
$R^6$ represents a $C_1$–$C_6$ alkyl group, a substituted $C_2$–$C_4$ alkyl group having at least one substituent selected from the group consisting of substituents (a′′′) or a $C_2$–$C_6$ alkenyl group;

substituents (a′′′):
$C_1$–$C_4$ alkoxy groups, $C_5$ or $C_6$ cycloalkyl groups, phenyl groups, substituted phenyl groups having at least one substituent selected from the group consisting of substituents (b′) and heterocyclic groups having 5 or 6 ring atoms; and substituents (b′):
$C_1$–$C_4$ alkyl groups, halogen atoms, the trifluoromethyl group and $C_1$–$C_4$ alkoxy groups;
and pharmaceutically acceptable acid addition salts thereof.

The compounds of the invention contain basic nitrogen atoms and hence can form acid addition salts. The nature of such salts is not critical to the present invention, except that, where the salts are to be used for therapeutic purposes, they must be pharmaceutically acceptable which, as is well known to those skilled in the art, means that the salts must not have an increased toxicity (or an unacceptably increased toxicity) or a reduced activity (or unacceptably reduced activity) as compared with the free bases. A wide variety of acids may be employed to form such salts and representative examples of such acids include: mineral acids, such as hydrochloric acid, hydrobromic acid, hydroiodic acid, phosphoric acid, metaphosphoric acid, nitric acid or sulfuric acid; and organic acids, such as acetic acid, oxalic acid, tartaric acid, citric acid, benzoic acid, glycolic acid, gluconic acid, glucuronic acid, succinic acid, maleic acid or fumaric acid. Such acid addition salts may be prepared by conventional methods.

The compounds of the present invention contain at least one (and may, depending on the nature of the substituent groups, contain more than one) asymmetric carbon atom and can thus exist in the form of various optical isomers. Although the various optical isomers are all represented herein by a single formula, the present invention embraces both the individual isolated isomers and mixtures thereof.

Examples of specific compounds of the invention are given in the following formula (I-1), in which the substituents are as defined in the corresponding Table 1. The compounds of the invention are hereinafter, where appropriate, identified by the numbers appended to them in these Tables. In the Tables, the following abbreviations are used:

| | |
|---|---|
| Ac | acetyl |
| All | allyl |
| Boz | benzoyl |
| Bu | butyl |
| iBu | isobutyl |
| Bz | benzyl |
| Byr | butyryl |
| iByr | isobutyryl |
| Bzc | benzyloxycarbonyl |
| Bzhy | benzhydryl |
| Car | carbamoyl |
| Cro | crotonoyl |
| Et | ethyl |
| Etc | ethoxycarbonyl |
| Fo | formyl |
| Fur | furyl |
| Furo | 2-furoyl |
| Hip | homopiperazinyl (= perhydro-1,4-diazepinyl) |
| Hpo | heptanoyl |
| Hx | hexyl |
| cHx | cyclohexyl |
| Me | methyl |
| Mec | methoxycarbonyl |
| Mes | methanesulfonyl |
| Mor | morpholino |
| Nic | nicotinoyl |
| iNic | isonicotinoyl |
| Ph | phenyl |
| Pic | picolinoyl |
| Pip | piperidyl |
| Piz | piperazinyl |
| Pr | propyl |
| iPr | isopropyl |
| Prn | propionyl |
| Pyr | pyridyl |
| Pyrd | pyrrolidinyl |
| Pyrr | pyrrolyl |
| Sam | sulfamoyl |
| Thi | thienyl |
| Thiz | thiazolyl |
| Thno | 2-thenoyl |
| Thz | perhydro-1,4-thiazin-4-yl (= thiomorpholino) |
| Tos | p-toluenesulfonyl |
| Ur | ureido |

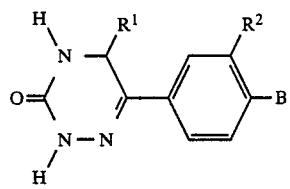

(I-1)

TABLE 1

| Cpd No. | $R^1$ | $R^2$ | B |
|---|---|---|---|
| 1 | Me | Cl | —OCH$_2$COOEt |
| 2 | H | F | —OCH$_2$COOH |
| 3 | Me | Br | —OCH$_2$COOPh |
| 4 | H | Cl | —OCH$_2$COOBz |
| 5 | Me | Me | —OCH$_2$CONHEt |
| 6 | H | —CF$_3$ | —OCH$_2$CONHBu |
| 7 | H | Cl | —OCH$_2$CONH$_2$ |
| 8 | H | ClCH$_2$— | —OCH$_2$CONHcHx |
| 9 | Me | NO$_2$ | —OCH$_2$CONH(2-MorEt) |
| 10 | H | NH$_2$ | —OCH$_2$CONH(2-MorEt) |
| 11 | Me | NMe$_2$ | —OCH$_2$CONH(1-Et-4-Pip) |
| 12 | H | NHMe | —OCH$_2$CONH(2-MorEt) |
| 13 | Me | Cl | —OCH$_2$CON(Me)cHx |
| 14 | H | CN | —OCH$_2$CONH(2-MorEt) |
| 15 | Me | Car | —OCH$_2$CONH(3-ClPr) |
| 16 | H | diMeCar | —OCH$_2$CONH(3-MeOPr) |
| 17 | Me | MeCar | —OCH$_2$CONH(3-HOPr) |
| 18 | H | 3-MeUr | —OCH$_2$CH$_2$CONH(4-PhOBu) |
| 19 | Me | MeOCO— | —OCH$_2$CH$_2$CONH(4-BzOBu) |
| 20 | H | Cl | —OCH$_2$CONH(2-EtOEt) |
| 21 | Me | F | —OCH$_2$CONH(3-MorPr) |
| 22 | H | F | —OCH$_2$CONH[2-(4-Nic-1-Piz)Et] |
| 23 | Me | —CF$_3$ | —OCH$_2$CONH(3-MorPr) |
| 24 | H | NHAc | —OCH$_2$CONH(2-MorEt) |
| 25 | Et | Cl | —OCH$_2$CONH[2-(2-Pyr)Et] |

TABLE 1-continued

| Cpd No. | R¹ | R² | B |
|---|---|---|---|
| 26 | Pr | Cl | —OCH₂CONH[2-(4-Ac-1-Piz)Et] |
| 27 | Bu | Cl | —OCH₂CONH[2-(4-Ac-1-Piz)Et] |
| 28 | H | F | —OCH₂CONH[2-(4-Me-1-Piz)Et] |
| 29 | H | F | —OCH₂CONH[2-(4-Ac-1-Piz)Et] |
| 30 | H | F | —OCH₂CONH[2-(4-Mes-1-Piz)Et] |
| 31 | H | Me | —OCH₂CONH(3-MorPr) |
| 32 | H | Cl | —OCH₂CON(Me)cHx |
| 33 | H | Me | —OCH₂CH₂CONHNH(2-MorEt) |
| 34 | H | Cl | —OCH₂CONHEt |
| 35 | Me | Cl | —OCH₂CONHMe |
| 36 | Me | Cl | —OCH₂CONHEt |
| 37 | Me | Cl | —OCH₂CONH₂ |
| 38 | H | Cl | —OCH₂CONHPr |
| 39 | H | Cl | —OCH₂CONHBu |
| 40 | H | Cl | —OCH₂CONHiBu |
| 41 | Me | Cl | —OCH₂CONHPr |
| 42 | Me | Cl | —OCH₂CONHHx |
| 43 | Me | Cl | —OCH(Et)CONHBu |
| 44 | H | Cl | —OCH₂CONH(2-MeOEt) |
| 45 | H | Cl | —OCH₂CONH(2-ThzEt) S-oxide |
| 46 | H | Cl | —OCH₂CONH(3-EtOPr) |
| 47 | H | Me | —OCH₂CONH(2-EtOEt) |
| 48 | H | F | —OCH₂CONH(2-EtOEt) |
| 49 | H | Br | —OCH₂CONH(2-MeOEt) |
| 50 | H | Cl | —OCH₂CH₂CONH[2-(4-Et-1-Piz)Et] |
| 51 | Me | Cl | —OCH₂CONH(2-MeOEt) |
| 52 | H | F | —OCH₂CONBu₂ |
| 53 | Me | Me | —OCH₂CONH(2-MeOEt) |
| 54 | Me | Cl | —OCH₂CONH(2-EtOEt) |
| 55 | Me | Cl | —OCH₂CONH(3-EtOPr) |
| 56 | Me | Cl | —OCH(Me)CONH(2-EtOEt) |
| 57 | Me | Cl | —OCH₂CONH(2-HOEt) |
| 58 | Me | Cl | —OCH₂CONH(2-PhOEt) |
| 59 | H | Cl | —OCH₂CONH(2-ThzEt) |
| 60 | Me | Cl | —OCH₂CONEt₂ |
| 61 | Me | Cl | —OCH₂CONPr₂ |
| 62 | Me | Cl | —OCH₂CONBu₂ |
| 63 | H | Cl | —OCH₂CON(Me)cHx |
| 64 | H | Cl | —OCH₂CONH(3-ThzPr) |
| 65 | Me | Cl | —OCH₂CONH(2-ClEt) |
| 66 | Me | Cl | —OCH₂CONH(3-ClPr) |
| 67 | Me | Cl | —OCH₂CONHBz |
| 68 | Me | Cl | —OCH₂CONH(4-ClBz) |
| 69 | Me | Cl | —OCH₂CONH(4-MeOBz) |
| 70 | Me | Cl | —OCH₂CONH(3-MeOBz) |
| 71 | Me | Cl | —OCH₂CONH(2-MeOBz) |
| 72 | H | Cl | —OCH₂CONH(2-PhEt) |
| 73 | Me | Cl | —OCH₂CONH(2-PhEt) |
| 74 | H | Me | —OCH₂CONH(2-PhEt) |
| 75 | Me | Me | —OCH₂CONH(2-PhEt) |
| 76 | H | F | —OCH₂CONH(2-PhEt) |
| 77 | H | F | —OCH₂CONH(2-ThzEt) |
| 78 | Me | Br | —OCH₂CONH(2-ThzEt) |
| 79 | H | Cl | —OCH₂CONH[2-(4-MeOPh)Et] |
| 80 | Me | Cl | —OCH₂CONH[2-(4-MeOPh)Et] |
| 81 | H | Cl | —OCH₂CONH[2-(2-MeOPh)Et] |
| 82 | H | Cl | —OCH₂CONH[2-(3,4-diMeOPh)Et] |
| 83 | Me | Cl | —OCH₂CONH[2-(3,4-diMeOPh)Et] |
| 84 | H | Cl | —OCH₂CONH[2-(4-ClPh)Et] |
| 85 | Me | Cl | —OCH₂CONH[2-(4-ClPh)Et] |
| 86 | Me | Cl | —OCH₂CONH[2-(2-ClPh)Et] |
| 87 | Me | Cl | —OCH₂CONH[2-(4-MePh)Et] |
| 88 | H | Cl | —OCH₂CONH(3-PhPr) |
| 89 | Me | Cl | —OCH₂CONH(4-PhBu) |
| 90 | Me | Cl | —OCH₂CONH[2-(NEt₂)Et] |
| 91 | H | Cl | —OCH₂CONH{2-[4-(2,4-diClBoz)-1-Piz]Et} |
| 92 | H | Cl | —OCH₂CONH[2-(2-Pyr)Et] |
| 93 | Me | Cl | —OCH₂CONH[2-(2-Pyr)Et] |
| 94 | Me | Me | —OCH₂CONH[2-(2-Pyr)Et] |
| 95 | H | Cl | —OCH₂CONH(2-MorEt) |
| 96 | Me | Cl | —OCH₂CONH(2-MorEt) |
| 97 | Me | F | —OCH₂CONH(2-MorEt) |
| 98 | Me | Me | —OCH₂CONH(2-MorEt) |
| 99 | H | NO₂ | —OCH₂CONH(2-MorEt) |
| 100 | Me | NHAc | —OCH₂CONH(2-MorEt) |
| 101 | Me | CN | —OCH₂CONH(2-MorEt) |
| 102 | H | Cl | —OCH₂CONH(3-MorPr) |
| 103 | Me | Cl | —OCH₂CONH(3-MorPr) |
| 104 | Me | Cl | —OCH₂CONH(2-ThzEt) |
| 105 | Me | Cl | —OCH₂CONH(2-ThzEt) S-oxide |
| 106 | Me | Cl | —OCH₂CONH(2-ThzEt) S,S-dioxide |
| 107 | H | Cl | —OCH₂CONH[2-(2,6-diMeMor)Et] |
| 108 | Me | Cl | —OCH₂CONH(2-MorEt) N-oxide |
| 109 | Me | Cl | —OCH₂CONH[2-(3-oxoMor)Et] |
| 110 | H | Cl | —OCH₂CONH[2-(3-oxoMor)Et] |
| 111 | Me | Cl | —OCH₂CONH[2-(1-Pyrd)Et] |
| 112 | Me | Cl | —OCH₂CONH[2-(1-Pip)Et] |
| 113 | Me | Cl | —OCH₂CONH[2-(1-Piz)Et] |
| 114 | H | Cl | —OCH₂CONH[2-(4-Me-1-Piz)Et] |
| 115 | Me | Cl | —OCH₂CONH[2-(4-Me-1-Piz)Et] |
| 116 | Me | Me | —OCH₂CONH[2-(4-Me-1-Piz)Et] |
| 117 | H | Me | —OCH₂CONH[2-(4-Me-1-Piz)Et] |
| 118 | H | Cl | —OCH₂CONH{2-[4-(2-HOEt)-1-Piz]Et} |
| 119 | H | Cl | —OCH₂CONH[2-(4-Ph-1-Piz)Et] |
| 120 | Me | Cl | —OCH₂CONH[2-(4-Ph-1-Piz)Et] |
| 121 | Me | Cl | —OCH₂CONH{2-[4-(4-ClPh)-1-Piz]Et} |
| 122 | Me | Cl | —OCH₂CONH{2-[4-(4-MeOPh)-1-Piz]Et} |
| 123 | Me | Cl | —OCH₂CONH{2-[4-(3-CF₃Ph)-1-Piz]Et} |
| 124 | Me | Cl | —OCH₂CONH{2-[4-(3-MePh)-1-Piz]Et} |
| 125 | H | Cl | —OCH₂CONH{2-[4-(2-Pyr)-1-Piz]Et} |
| 126 | Me | Cl | —OCH₂CONH{2-[4-(2-Pyr)-1-Piz]Et} |
| 127 | Me | NO₂ | —OCH₂CONH{2-[4-(2-Pyr)-1-Piz]Et} |
| 128 | Me | NHAc | —OCH₂CONH{2-[4-(2-Pyr)-1-Piz]Et} |
| 129 | Me | Car | —OCH₂CONH{2-[4-(2-Pyr)-1-Piz]Et} |
| 130 | Me | Cl | —OCH₂CONH[2-(4-Bz-1-Piz)Et] |
| 131 | H | Cl | —OCH₂CONH[2-(4-Bz-1-Piz)Et] |
| 132 | H | Cl | —OCH₂CONH[2-(4-Bzhy-1-Piz)Et] |
| 133 | Me | Cl | —OCH₂CONH[2-(4-Bzhy-1-Piz)Et] |
| 134 | Me | Cl | —OCH₂CONH{2-[4-(4-ClBzhy)-1-Piz]Et} |
| 135 | Me | Cl | —OCH₂CONH{2-[4-(4,4'-diFBzhy)-1-Piz]Et} |
| 136 | Me | Cl | —OCH₂CONH{2-[4-(4,4-diPhBu)-1-Piz]Et} |
| 137 | Me | Cl | —OCH₂CONH[2-(4-Fo-1-Piz)Et] |
| 138 | Me | Cl | —OCH₂CONH[2-(4-Ac-1-Piz)Et] |
| 139 | H | Cl | —OCH₂CONH[2-(4-Ac-1-Piz)Et] |
| 140 | H | Cl | —OCH₂CONH[2-(4-Prn-1-Piz)Et] |
| 141 | Me | Cl | —OCH₂CONH[2-(4-Prn-1-Piz)Et] |
| 142 | H | Cl | —OCH₂CONH[2-(4-iByr-1-Piz)Et] |
| 143 | Me | Cl | —OCH₂CONH[2-(4-iByr-1-Piz)Et] |
| 144 | H | Cl | —OCH₂CONH[2-(4-HPo-1-Piz)Et] |
| 145 | Me | Cl | —OCH₂CONH[2-(4-HPo-1-Piz)Et] |
| 146 | Me | Cl | —OCH₂CONH[2-(4-Cro-1-Piz)Et] |
| 147 | Me | Cl | —OCH₂CONH{2-[4-(4-ClByr)-1-Piz]Et} |
| 148 | Me | Cl | —OCH₂CONH{2-[4-(EtOAc)-1-Piz]Et} |
| 149 | H | Cl | —OCH₂CONH[2-(4-Etc-1-Piz)Et] |
| 150 | Me | Cl | —OCH₂CONH[2-(4-Bzc-1-Piz)Et] |
| 151 | Me | Cl | —OCH₂CONH{2-[4-(3-PhPrn)-1-Piz]Et} |
| 152 | H | Cl | —OCH₂CONH[2-(4-Boz-1-Piz)Et] |
| 153 | Me | Cl | —OCH₂CONH[2-(4-Boz-1-Piz)Et] |
| 154 | Me | F | —OCH₂CONH[2-(4-Boz-1-Piz)Et] |
| 155 | Me | Cl | —OCH₂CONH{2-[4-(4-ClBoz)-1-Piz]Et} |
| 156 | H | Cl | —OCH₂CONH{2-[4-(3,5-diMeOBoz)-1-Piz]Et} |
| 157 | Me | Cl | —OCH₂CONH{2-[4-(4-MeOBoz)-1-Piz]Et} |
| 158 | Me | Cl | —OCH₂CONH{2-[4-(2-MeOBoz)-1-Piz]Et} |
| 159 | Me | Cl | —OCH₂CONH{2-[4-(4-MeBoz)-1-Piz]Et} |
| 160 | Me | F | —OCH₂CONH{2-[4-(4-MeBoz)-1-Piz]Et} |
| 161 | H | Cl | —OCH₂CONH[2-(4-Mes-1-Piz)Et] |
| 162 | Me | Cl | —OCH₂CONH[2-(4-Mes-1-Piz)Et] |

TABLE 1-continued

| Cpd No. | R¹ | R² | B |
|---|---|---|---|
| 163 | Me | Cl | —OCH₂CONH[2-(4-Tos-1-Piz)Et] |
| 164 | H | Cl | —OCH₂CONH[2-(4-Pic-1-Piz)Et] |
| 165 | Me | Cl | —OCH₂CONH[2-(4-Pic-1-Piz)Et] |
| 166 | H | NO₂ | —OCH₂CONH[2-(4-Pic-1-Piz)Et] |
| 167 | Me | Cl | —OCH₂CONH[2-(4-Furo-1-Piz)Et] |
| 168 | H | Cl | —OCH₂CONH[2-(4-Furo-1-Piz)Et] |
| 169 | H | Cl | —OCH₂CONH[2-(4-Thno-1 Piz)Et] |
| 170 | Me | Cl | —OCH₂CONH[2-(4 Thno-1-Piz)Et] |
| 171 | Me | Cl | —OCH₂CONH{2-[4-(4-Cl-3-SamBoz-1-Piz]Et} |
| 172 | Me | Me | —OCH₂CONH{2-[4-(4-Cl-3-SamBoz-1-Piz]Et} |
| 173 | H | Cl | —OCH₂CONH[2-(4-MeCar-1-Piz)Et] |
| 174 | Me | Cl | —OCH₂CONH[2-(4-MeCar-1-Piz)Et] |
| 175 | H | Cl | —OCH₂CONH{2-[4-(4-ClPh)-1-Piz]Et} |
| 176 | H | Cl | —OCH₂CONH{2-[4-(3-MePh)-1-Piz]Et} |
| 177 | H | Cl | —OCH₂CONH{2-[4-(3-MeOPh)-1-Piz]Et} |
| 178 | Me | Cl | —OCH₂CONH{2-[4-(3-MeOPh)-1-Piz]Et} |
| 179 | Me | Cl | —OCH₂CONH{2-[4-(2-MeOPh)-1-Piz]Et} |
| 180 | Me | Cl | —OCH₂CONH[2-(4-Ac-2-oxo-1-Piz)Et] |
| 181 | Me | Cl | —OCH₂CONH[2-(3-oxo-1-Piz)Et] |
| 182 | Me | Cl | —OCH₂CONH[2-(4-Prn-2-oxo-1-Piz)Et] |
| 183 | Me | Cl | —OCH₂CONH[2-(4-Boz-2-oxo-1-Piz)Et] |
| 184 | H | Cl | —OCH₂CONH[2-(4-Nic-1-Piz)Et] |
| 185 | H | Cl | —OCH₂CONHAll |
| 186 | Me | Cl | —OCH₂CONHcHx |
| 187 | Me | Cl | —OCH₂CONH(2-Pyr) |
| 188 | Me | Cl | —OCH₂CONH(2-Thiz) |
| 189 | Me | Cl | —OCH₂CONH(1-Bz-4-Pip) |
| 190 | H | Me | —OCH₂CONH(1-Me-4-Pip) |
| 191 | Me | Me | —OCH₂CONH(1-Me-4-Pip) |
| 192 | Me | Cl | —OCH₂CONH(1-Me-4-Hip) |
| 193 | H | Cl | —OCH₂CONH(1-Me-4-Hip) |
| 194 | H | Cl | —OCH₂CONH(1-Ac-4-Hip) |
| 195 | Me | Cl | —OCH₂CONHNH₂ |
| 196 | Me | Cl | —OCH₂CONHNHPh |
| 197 | Me | Cl | —OCH₂CONH(2,5-diMe-1-Pyrr) |
| 198 | Me | Cl | —OCH₂CONH(1-Pip) |
| 199 | Me | Cl | —OCH₂CONHMor |
| 200 | Me | Cl | —OCH₂CONHNH(2-MorEt) |
| 201 | Me | Cl | —OCH₂COMor |
| 202 | H | Cl | —OCH₂CONHNH[2-(1-Pyrd)Et] |
| 203 | H | Cl | —OCH₂CONHNH[2-(1-Pip)Et] |
| 204 | H | Cl | —OCH₂CONHNH(2-MorEt) |
| 205 | Me | Cl | —OCH₂CO(4-Me-1-Piz) |
| 206 | H | Cl | —OCH₂CONPr₂ |
| 207 | H | Cl | —OCH₂CONBu₂ |
| 208 | H | Cl | —OCH₂CONiBu₂ |
| 209 | H | Me | —OCH₂CONH(2-MorEt) |
| 210 | H | Me | —OCH₂CONH[2-(4-Ac-1-Piz)Et] |
| 211 | H | Me | —OCH₂CONBu₂ |
| 212 | H | Me | —OCH₂CONH[2-(4-Boz-1-Piz)Et] |
| 213 | H | Cl | —OCH₂CONH[2-(4-iNic-1-Piz)Et] |
| 214 | H | Me | —OCH₂CONH[2-(4-iNic-1-Piz)Et] |
| 215 | H | Me | —OCH₂CONH(2-ThzEt) |
| 216 | H | NO₂ | —OCH₂CONH(2-ThzEt) |
| 217 | H | NO₂ | —OCH₂CONH[2-(4-Ac-1-Hip)Et] |
| 218 | H | NO₂ | —OCH₂CONH{2-[4-(2-Fur)-1-Piz]Et} |
| 219 | H | —NHAc | —OCH₂CONBu₂ |
| 220 | H | H | —OCH₂CONH(2-MorEt) |
| 221 | Me | H | —OCH₂CONH(2-MorEt) |
| 222 | H | H | —SCH₂CONH(2-MorEt) |
| 223 | H | H | —OCH(Et)CONH(2-MorEt) |
| 224 | H | H | —OCH₂CONH(2-ThzEt) |
| 225 | H | H | —OCH₂CONH[2-(1-Pip)Et] |
| 226 | H | H | —OCH₂CONH[2-(4-Me-1-Piz)Et] |
| 227 | H | H | —OCH₂CONH{2-[4-(2-Pyr)-1-Piz]Et} |
| 228 | Me | H | —OCH₂CONH{2-[4-(2-Pyr)-1-Piz]Et} |
| 229 | H | H | —OCH₂CONH[2-(4-Ph-1-Piz)Et] |
| 230 | H | H | —OCH₂CONH{2-[4-(2-ClPh)-1-Piz]Et} |
| 231 | H | H | —OCH₂CONH{2-[4-(4-ClPh)-1-Piz]Et} |
| 232 | H | H | —OCH₂CONH[2-(4-Prn-1-Piz)Et] |
| 233 | H | H | —OCH₂CONH[2-(4-Etc-1-Piz)Et] |
| 234 | Me | H | —OCH₂CONH[2-(4-Etc-1-Piz)Et] |
| 235 | Me | Cl | —OCH₂CONHCH(Etc)Bz |
| 236 | H | Cl | —OCH₂CONHCH(Bz)CONH(2-MorEt) |
| 237 | Me | Cl | —OCH₂CONHCH(Mec)(2-Thi) |
| 238 | H | Me | —OCH₂CONHCH(Bz)CONHMe |
| 239 | H | H | —OCH₂CONHCH(Etc)CH₂(3-Pyr) |
| 240 | H | Cl | —OCH₂CONHCH(Etc)Bz |
| 241 | H | Me | —OCH₂CONHCH(Etc)Bz |
| 242 | H | Cl | —OCH₂CONHCH(Ph)CONH(2-MorEt) |
| 243 | Me | Cl | —OCH₂CONHCH(Ph)CONH(2-MorEt) |
| 244 | H | Cl | —OCH₂CONHCH(Etc)(2-Thi) |
| 245 | H | H | —OCH₂CONHCH(Mec)(3-Pyr) |
| 246 | H | Me | —OCH₂CONHCH(Bz)COO{2-[N(Me)Bz]Et} |
| 247 | H | Cl | —OCH₂CONHCH(iBu)CONH(2-MorEt) |
| 248 | H | Cl | —OCH₂CONHCH(iPr)CONH(2-MorEt) |
| 249 | H | Cl | —OCH₂CON[2-(3-oxoMor)Et] |

Of the compounds listed above, the following are most preferred:

40. α-[2-Chloro-4-(2,3,4,5-tetrahydro-5-methyl-3-oxo-1,2,4-triazin-6-yl)phenoxy]-N-isobutylacetamide.
41. α-[2-Chloro-4-(2,3,4,5-tetrahydro-5-methyl-3-oxo-1,2,4-triazin-6-yl)phenoxy]-N-propylacetamide.
54. α-[2-Chloro-4-(2,3,4,5-tetrahydro-5-methyl-3-oxo-1,2,4-triazin-6-yl)phenoxy]-N-(2-ethoxyethyl)-acetamide.
55. α-[2-Chloro-4-(2,3,4,5-tetrahydro-5-methyl-3-oxo-1,2,4-triazin-6-yl)phenoxy]-N-(3-ethoxypropyl)-acetamide.
72. α-[2-Chloro-4-(2,3,4,5-tetrahydro-3-oxo-1,2,4-triazin-6-yl)phenoxy]-N-phenethylacetamide.
73. α-[2-Chloro-4-(2,3,4,5-tetrahydro-5-methyl-3-oxo-1,2,4-triazin-6-yl)phenoxy]-N-phenethylacetamide.
83. α-[2-Chloro-4-(2,3,4,5-tetrahydro-5-methyl-3-oxo-1,2,4-triazin-6-yl)phenoxy]-N-[2-(3,4-dimethoxyphenyl)ethyl]acetamide.
95. α-[2-Chloro-4-(2,3,4,5-tetrahydro-3-oxo-1,2,4-triazin-6-yl)phenoxy]-N-(2-morpholinoethyl)-acetamide.
96. α-[2-Chloro-4-(2,3,4,5-tetrahydro-5-methyl-3-oxo-1,2,4-triazin-6-yl)phenoxy]-N-(2-morpholinoethyl)-acetamide.
155. α-[2-Chloro-4-(2,3,4,5-tetrahydro-5-methyl-3-oxo-1,2,4-triazin-6-yl)phenoxy]-N-{2-[4-(4-chlorobenzoyl)-1-piperazinyl]ethyl}acetamide.
162. α-[2-Chloro-4-(2,3,4,5-tetrahydro-5-methyl-3-oxo-1,2,4-triazin-6-yl)phenoxy]-N-[2-(4-methanesulfonyl-1-piperazinyl)ethyl]acetamide.
189. α-[2-Chloro-4-(2,3,4,5-tetrahydro-5-methyl-3-oxo-1,2,4-triazin-6-yl)phenoxy]-N-(1-benzyl-4-piperidyl)acetamide.

Also preferred are the pharmaceutically acceptable acid addition salts of the above compounds.

In general terms, the compounds of the present invention may be prepared from a compound of formula (II):

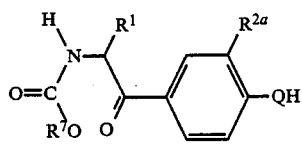

(II)

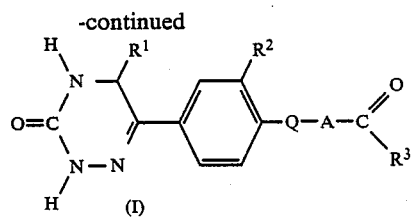

In the above formulae:

$R^1$, $R^2$, $R^{2a}$, $R^3$, $R^7$, A and Q are as defined above;

$R^{3a}$ represents any of the groups represented by $R^3$ but in which, if necessary, any active group is protected, and preferably represents the previously defined group of formula $-(NH)_n-NR^5R^6$; and X represents a halogen atom, for example a chlorine, bromine or iodine atom.

Examples of carboxy-protecting groups which may be represented by $R^7$ are given above in relation to the protected carboxy groups which may be represented by $R^2$.

Step A1:

In step A1 of Method A, a compound of formula (II) is converted to an alkali metal salt thereof and then reacted with a halo compound of formula (III):

$$X-A-COR^{3a} \qquad (III)$$

(in which $R^{3a}$, X and A are as defined above). Alternatively, said compound of formula (II) may be reacted directly with said halo compound of formula (III) in the presence of a base.

The reaction is preferably effected in the presence of a solvent, the nature of which is not critical, provided that it has no adverse effect upon the reaction. Suitable solvents include, for example: amides, such as dimethylformamide, dimethylacetamide or hexamethylphosphoric triamide; sulfoxides, such as dimethyl sulfoxide; ethers, such as tetrahydrofuran or dioxane; and nitriles, such as acetonitrile.

The alkali metal salt to which the compound of formula (II) may be converted is preferably a sodium, potassium or lithium salt. Conversion to this salt may be effected by treating the compound of formula (II) with an alkali metal compound, for example: an alkali metal hydride, such as sodium hydride or potassium hydride; or an organic lithium compound, such as lithium isobutyl cyclohexylamide or lithium dicyclohexylamide. This reaction may be effected over a wide range of temperatures, and the precise reaction temperature chosen is not critical to the invention. However, we generally find it convenient to carry out the reaction at a relatively low temperature, for example from $-20°$ C. to $50°$ C., more preferably to about ambient temperature. The time required for the reaction to produce the alkali metal salt will vary widely, depending upon many factors, including the reaction temperature and the nature of the reagents; however, a period of from 15 minutes to 2 hours will normally suffice.

Where the reaction is effected in the presence of a base, the nature of the base is not critical. Preferred bases include alkali metal carbonates and bicarbonates, such as sodium bicarbonate, potassium bicarbonate, sodium carbonate or potassium carbonate.

Reaction of the compound of formula (II) or the alkali metal salt thereof with the compound of formula (III) is preferably effected in one of the above solvents

[in which:

$R^1$ and Q are as defined above;

$R^{2a}$ represents any of the groups and atoms defined above for $R^2$ or any such group in which any active group is, if necessary, protected; and $R^7$ represents a carboxy-protecting group]

or an active equivalent thereof by:

(a) ring closure to form the triazinone ring by reaction with hydrazine or an active derivative thereof;

(b) introduction of a group of formula $-A-CO-R^3$ at the 4-position of the benzene ring; and (c) if necessary, any one or more of deprotection and salification;

the reactions of steps (a), (b) and (c) being carried out in any appropriate order.

In step (b), the desired group of formula $-A-CO-R^3$ may be introduced directly into the 4-position or a different group may be introduced initially and then converted in a subsequent reaction at any stage to the desired group.

In more detail, the process of the present invention may be carried out as described in any of the following Methods A and B:

Method A:

Compounds of the invention may be prepared as illustrated by the following reaction scheme:

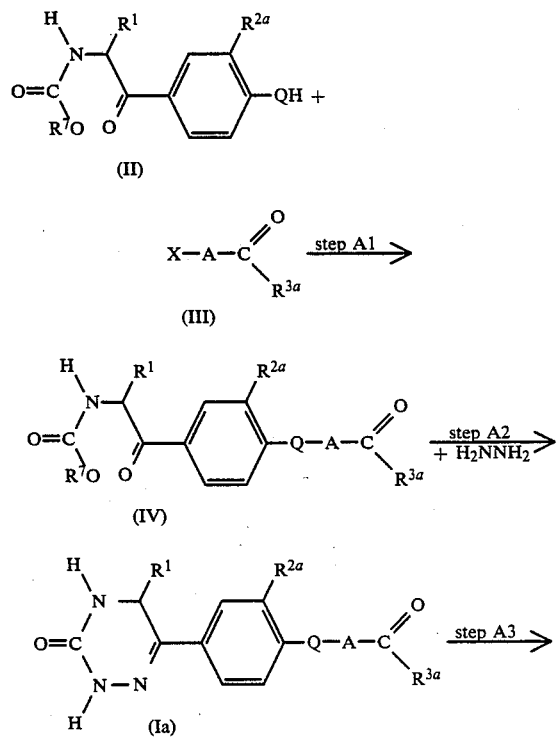

and more preferably in the same reaction mixture as was used to produce the salt, without intermediate isolation. This reaction may be effected over a wide range of temperatures, and the precise reaction temperature chosen is not critical to the invention. However, we generally find it convenient to carry out the reaction at a temperature of from 0° C. to 120° C., more preferably from about ambient temperature to the boiling temperature of the solvent employed. The time required for the reaction may vary widely, depending upon many factors, primarily the reaction temperature, but a period of from 5 minutes to 2 days, more commonly from 30 minutes to 5 hours, will normally suffice.

The relative proportions of the compound of formula (II) or the alkali metal salt thereof and the compound of formula (III) may vary widely, although approximately stoichiometric amounts are preferred. Although the reaction may be accelerated by employing an excess of the compound of formula (III), this can result in the introduction of a group of formula —A—COR$^{3a}$ as a substituent on one of the nitrogen atoms of the triazinone system.

After completion of the reaction, the resulting compound of formula (IV) may be recovered from the reaction mixture by conventional means. For example, one suitable recovery technique comprises: distilling the solvent from the reaction mixture; mixing the residue with ice-water; extracting the mixture with a water-immiscible organic solvent; washing with water and then drying the extract; and finally distilling the solvent from the extract to give the desired product. If desired, this may be further purified by conventional techniques, for example recrystallization or the various chromatography techniques, particularly column chromatography.

Step A2:

In step A2 of this Method, the compound of formula (IV), obtained in step A1, is reacted with hydrazine in an inert solvent, to give the compound of formula (Ia).

The nature of the solvent employed in this process is not critical, provided that it has no adverse effect upon the reaction. Examples of suitable solvents include: alcohols, such as methanol, ethanol, propanol or butanol; ethers, such as diethyl ether or tetrahydrofuran; aromatic hydrocarbons, such as benzene, toluene, xylene or mesitylene; amides, especially fatty acid amides, such as dimethylformamide or dimethylacetamide; water; and mixtures of one or more of the above organic solvents with water. Of these, we prefer the alcohols.

The reaction will take place over a wide range of temperatures, but we generally find it convenient to carry out the reaction at a temperature of from 0° to 150° C. preferably up to 100° C. more preferably from ambient temperature to the boiling temperature of the solvent employed, and most preferably either at ambient temperature or at or about the boiling temperature of the solvent employed. The time required for the reaction will vary, depending upon many factors, notably the reaction temperature and the nature of the reagents, but a period of from 2 to 6 days, more often from 2 hours to 10 hours, will normally suffice.

After completion of the reaction, the desired compound of formula (Ia) may be recovered from the reaction mixture by conventional means. For example, one suitable recovery procedure comprises: pouring the reaction mixture into ice-water, optionally after distilling off the solvent; extracting the mixture with a water-immiscible organic solvent; washing the extract with water and drying it; and finally distilling the solvent from the extract. If necessary, this product may be further purified by such conventional techniques as recrystallization or the various chromatography techniques, particularly column chromatography.

The compound of formula (Ia) obtained in step A2 may be a compound of the invention and may be the desired final product. Alternatively, it may, if desired, be subjected to one or more of the reactions which, together, are represented by step A3.

Step A3:

The reactions represented by step A3 in the above reaction scheme are optional and include the following series of reactions, which, where two or more are to be employed, may be selected and combined in any appropriate order:

A3(a) conversion of a carboxy group or an ester residue to an amide group;

A3(b) removal of any protecting group;

A3(c) addition of a suitable protecting group, where required;

A3(d) replacement of hydrogen atoms of amino groups and/or imino groups in the molecule;

A3(e) conversion of a nitro group into an amino group and optionally conversion of such an amino group into a mono- or di- alkylamino group;

A3(f) conversion of a terminal hydrazino group into a pyrrolyl group;

A3(g) N-oxidation, S-oxidation or S,S-dioxidation;

A3(h) ester hydrolysis;

A3(i) conversion of a carboxy group to an ester group;

A3(j) salification.

A3(a) Conversion of a carboxy group or an ester residue to an amide group

In this step, where R$^{3a}$ represents a hydroxy group or an ester residue, the compound of formula (Ia)— before or after it has been subjected to any one or more of the other optional reactions of step A3—is reacted with an amine compound of formula (V):

$$H\text{-}R^{3b} \qquad\qquad (V)$$

[in which R$^{3b}$ represents said group of formula —(NH-)$_n$—NR$^5$R$^6$, in which R$^5$, R$^6$ and n are as defined above], to give the desired compound of formula (I) where R$^3$ is an amide residue.

The reaction with the amine compound of formula H-R$^{3b}$ is preferably effected in the presence of an inert solvent, although it may also be effected without any solvent. The nature of the solvent is not critical, provided that it has no adverse effect upon the reaction. Suitable solvents include, for example: any of the solvents suggested for use in step A1; or an alcohol, such as methanol, ethanol, propanol or butanol.

This reaction may be effected over a wide range of temperatures, and the precise reaction temperature chosen is not critical to the invention. However, when R$^{3a}$ represents a carboxy-protecting group, preferably the residue of an ester, we generally find it convenient to carry out the reaction at a temperature of from 0° C. to 150° C. and more preferably from ambient temperature to the boiling temperature of the solvent employed. The time required for the reaction may vary widely, depending upon many factors, primarily the reaction temperature, but a period of from 30 minutes to 4 days will normally suffice.

When $R^{3a}$ represents a hydroxy group, we generally find it convenient to carry out the reaction at a temperature of from 0° C. to 50° C. The time required for the reaction may vary widely, depending upon many factors, primarily the reaction temperature, but a period of from 2 to 24 hours will normally suffice. This reaction is also preferably effected in the presence of a dehydrating agent. The nature of the dehydrating agent is not especially critical and any dehydrating agent commonly used in this type of reaction may equally be employed here. Preferred examples include: carbodiimides, such as dicyclohexylcarbodiimide; and esters of cyanophosphonic acid, such as diethyl cyanophosphonate or dimethyl cyanophosphonate. The esters of cyanophosphonic acid are preferred. The reaction is preferably carried out in the presence of a base. The nature of the base is not critical, although we prefer organic amines, such as triethylamine, pyridine or 4-dimethylaminopyridine.

This step can also be effected by converting the carboxylic acid into a reactive derivative thereof, and then allowing the resulting derivative to react with the amine compound of formula H-$R^{3b}$. Suitable reactive derivatives of the carboxylic acid include, for example: acid halides, such as the acid chloride; mixed acid anhydrides with another organic carboxylic acid such as acetic acid, propionic acid or pivalic acid; and active esters, such as the isobutoxycarbonyl ester. The reactive derivative can be prepared easily by such conventional means as treating the carboxylic acid with a halogen derivative such as thionyl chloride, acetyl chloride, pivaloyl chloride or isobutoxycarbonyl chloride.

The reaction of the amine compound of formula H-$R^{3b}$ with the reactive derivative is preferably effected in an inert solvent and in the presence of a base. The nature of the solvent is not critical, provided that it has no adverse effect upon the reaction. Suitable solvents include, for example: hydrocarbons, which may be aliphatic or aromatic, such as benzene or hexane; halogenated hydrocarbons, preferably halogenated aliphatic hydrocarbons, such as methylene chloride or chloroform; and ethers, such as diethyl ether or tetrahydrofuran. The base used may be any of those exemplified above. This reaction may be effected over a wide range of temperatures, and the precise reaction temperature chosen is not critical to the invention. However, we generally find it convenient to carry out the reaction at about ambient temperature. The time required for the reaction may vary widely, depending upon many factors, primarily the reaction temperature, but a period of from 30 minutes to 3 hours will normally suffice.

After completion of the reaction, the desired compound can be isolated from the reaction mixture by conventional means. If desired, the product can be further purified by such conventional purification procedures as recrystallizaiton, preparative thin layer chromatography and column chromatography.

A3(b) Removal of protecting groups

Removal of the amino-protecting groups and/or removal of the carboxy-protecting groups, if required, can be effected by any known method, although, as is well known, the precise method chosen will depend on the kind of protecting group, as explained below.

When the amino-protecting group is a lower aliphatic acyl group, an aromatic acyl group, or a lower alkoxycarbonyl group, it can be removed by treatment with an acid or a base in the presence of an aqueous solvent. There is no particular limitation on the nature of the solvent to be employed, and any solvent commonly used for hydrolysis may equally be employed in this reaction. Examples include: water; and mixtures of water with an organic solvent, for example, an alcohol (such as methanol, ethanol or propanol) or an ether (such as tetrahydrofuran or dioxane).

There is no particular limitation on the nature of the acid or base to be employed, and any acid or base commonly used for hydrolysis may equally be employed in this reaction. Examples of suitable acids include such mineral acids as hydrochloric acid, sulfuric acid, phosphoric acid and hydrobromic acid. Examples of suitable bases include such alkali metal and other hydroxides as sodium hydroxide, potassium hydroxide, barium hydroxide and ammonium hydroxide. However, as alkaline hydrolysis may sometimes bring about isomerization, acid hydrolysis is preferred and produces a good result.

The reaction will take place over a wide range of temperatures, but we generally find it convenient to carry out the reaction at a temperature of from room temperature to 100° C. The time required for the reaction will vary, depending upon many factors, notably the reaction temperature and the nature of the reagents, but a period of from 30 minutes to 10 hours will normally suffice.

When the amino-protecting group is an aralkyl group, it is preferred to remove the group by catalytic hydrogenation at room temperature, using a catalyst such as platinum or palladium-on-carbon in the presence of hydrogen. The reaction is preferably effected in the presence of a solvent. The nature of the solvent employed in this reaction is not particularly critical, provided that it has no adverse effect upon the reaction. Examples of suitable solvents include: alcohols, such as methanol or ethanol; ethers, such as tetrahydrofuran or dioxane; fatty acids, such as acetic acid; or a mixture of water with any one or more of these organic solvents.

The reaction will take place over a wide range of temperatures, but we generally find it convenient to carry out the reaction at a temperature of from 0 to room temperature. The time required for the reaction will vary, depending upon many factors, notably the reaction temperature, the nature of the reagents and the nature of the catalyst, but a period of from 5 minutes to 12 hours will normally suffice.

When the amino-protecting group is an alkenyloxycarbonyl group, it can be removed by treatment with an acid or a base in a similar manner to that employed to remove an amino-protecting group when that group is a lower aliphatic acyl group, an aromatic acyl group or a lower alkoxycarbonyl group. However, in particular when the protecting group is an allyloxycarbonyl group, deprotection using palladium and either triphenylphosphine or nickel tetracarbonyl is especially convenient, and the reaction can be carried out with very few side reactions.

Occasionally, the procedure used for removing the carboxy-protecting groups mentioned above may also remove the amino-protecting groups at the same time.

After completion of the reaction, the desired compound can be isolated from the reaction mixture by conventional means. Thereafter, if required, the product may be further purified by such conventional techniques as recrystallization or the various chromatography techniques, particularly preparative thin layer chromatography or column chromatography.

When the carboxy-protecting group is a lower alkyl group or an aryl group, it can be removed by treatment with an acid or a base. The reaction conditions are the same as those employed in the removal of amino-protecting groups when those groups are lower aliphatic acyl groups, aromatic acyl groups or lower alkoxycarbonyl groups.

When the carboxy-protecting group is an aralkyl group or a halogenated lower alkyl group, it can be removed by contact with a reducing agent. The preferred methods of reduction are: using zinc-acetic acid as a reducing agent, if the carboxy group is protected by a halogenated lower alkyl group; and catalytic reduction using a catalyst such as palladium-on-carbon or platinum in the presence of hydrogen, or treatment with an alkali metal sulfide, such as potassium sulfide or sodium sulfide, if it is protected by an aralkyl group. These reactions are normally carried out in the presence of a solvent. There is no particular restriction on the nature of the solvent to be employed, provided that it does not interfere with the reaction and that it can dissolve the starting materials at least to some extent. Examples of preferred solvents include: alcohols, such as methanol or ethanol; ethers, such as tetrahydrofuran or dioxane; fatty acids, such as acetic acid; and mixtures of any one or more thereof with water.

These reactions will take place over a wide range of temperatures and the precise temperature chosen is not particularly critical. We generally find it convenient to conduct the reactions at a temperature from 0° C. to about room temperature. The time required for the reactions may vary widely, depending on many factors, notably the reaction temperature and the nature of the starting materials employed, but a period of from 5 minutes to 12 hours will normally suffice.

When the carboxy-protecting group is an alkoxymethyl group, it can be removed by treatment with an acid. Preferred acids include: hydrochloric acid; and mixtures of acetic acid with sulfuric acid. The reaction is normally carried out in the presence of a solvent. There is no particular restriction on the nature of the solvent to be employed, provided that it does not interfere with the reaction and that it can dissolve the starting materials at least to some extent. Examples of preferred solvents include: alcohols, such as methanol or ethanol; ethers, such as tetrahydrofuran or dioxane; and mixtures of any one or more thereof with water.

The reaction will take place over a wide range of temperatures and the precise temperature chosen is not particularly critical. We generally find it convenient to conduct the reaction at a temperature from 0° C. to 50° C. The time required for the reaction may vary widely, depending on many factors, notably the reaction temperature and the nature of the starting materials and base employed, but a period of from 10 minutes to 18 hours will normally suffice.

Occasionally, the procedure employed to remove the carboxy-protecting group as described above may also remove the amino-protecting groups at the same time.

After completion of the reaction, the desired compound can be separated from the reaction mixture by conventional means. For example, one suitable recovery technique comprises: filtering off the insoluble material which separates from the reaction mixture; washing and then drying the organic layer; and finally distilling off the organic solvent. The compound can then, if desired, be further purified by such conventional purification methods as recrystallization, preparative thin layer chromatography and column chromatography.

The order in which amino-protecting groups and carboxy-protecting groups are removed is not critical, and the various reactions described above can be carried out in any desired order.

A3(c) Addition of protecting groups

If desired, the carboxy group can be protected again by any one of the protecting groups described above which are capable of being hydrolyzed in vivo. This reaction may be carried out by conventional means well known in this field. For example, an ester derivative in which the carboxy group is protected by a protecting group capable of being hydrolyzed in vivo can be prepared by reaction with: an aliphatic acyloxymethyl halide such as acetoxymethyl chloride, propionyloxymethyl bromide or pivaloyloxymethyl chloride; a ($C_1$–$C_6$ alkoxy)carbonyloxyethyl halide, such as 1-methoxycarbonyloxyethyl chloride or 1-ethoxycarbonyloxyethyl iodide; a phthalidyl halide; or a (2-oxo-5-methyl-1,3-dioxolen-4-yl)methyl halide. The reaction is normally carried out in the presence of a solvent. There is no particular restriction on the nature of the solvent to be employed, provided that it does not interfere with the reaction and that it can dissolve the starting materials at least to some extent. Examples of preferred solvents include polar solvents, such as dimethylformamide.

The reaction will take place over a wide range of temperatures and the precise temperature chosen is not particularly critical. We generally find it convenient to conduct the reaction at a temperature from 0° C. to 100° C. However, in the case of the (2-oxo-5-methyl-1,3-dioxolen-4-yl)methyl halides, the preferred reaction temperature is from 0° C. to 50° C. The time required for the reaction may vary widely, depending on many factors, notably the reaction temperature and the nature of the starting materials employed, but a period of from 30 minutes to 10 hours will normally suffice.

A3(d) Replacement of hydrogen atoms of amino groups and/or imino groups

Where the group $R^3$ or $R^{3a}$ in the resulting compound contains an amino or imino group, the hydrogen atom(s) of such a group may be replaced by a variety of groups. Examples of such groups which may replace amino or imino hydrogen atoms include: lower alkyl groups; aralkyl groups; lower aliphatic acyl groups; aromatic acyl groups; aralkylcarbonyl groups; aromatic heterocyclic carbonyl groups; lower alkoxycarbonyl groups; aralkyloxycarbonyl groups; lower alkylsulfonyl groups; arylsulfonyl groups; and carbamoyl groups which may be substituted by one or two lower alkyl groups.

The reagent employed to introduce such a group is preferably one in which a nucleophilic leaving group or atom is combined with any one of the groups mentioned above. Suitable nucleophilic leaving groups or atoms include, for example, halogen atoms and acyloxy groups. The reaction can be carried out by conventional means, preferably in an inert solvent. There is no particular restriction on the nature of the solvent to be employed, provided that it does not interfere with the reaction and that it can dissolve the starting materials at least to some extent. Examples of preferred solvents include: amides, such as dimethylformamide or dimethylacetamide; sulfoxides such as dimethyl sulfoxide; alcohols, such as methanol or ethanol; water; and mixtures of water with any one or more of the organic solvents mentioned above.

The reaction will take place over a wide range of temperatures and the precise temperature chosen is not particularly critical. We generally find it convenient to conduct the reaction at a temperature from 0° C. to 100° C. or to the boiling temperature of the solvent employed. The time required for the reaction may vary widely, depending on many factors, notably the reaction temperature and the nature of the starting materials employed, but a period of from 30 minutes to 24 hours will normally suffice.

The reaction may be conducted in the presence or absence of an inorganic or organic base, but the presence of a base may be advantageous, since its presence accelerates the reaction rate. Examples of suitable bases include such inorganic bases as sodium bicarbonate, potassium bicarbonate, sodium carbonate or potassium carbonate, and such organic bases as triethylamine or pyridine.

For example, alkylation may be effected by reacting the compound with an alkyl halide, such as methyl iodide, ethyl iodide or benzyl bromide. Acylation may be effected by reacting the compound with an acid halide or acid anhydride, such as acetyl chloride, acetic anhydride, propionyl bromide, benzoyl chloride, p-chlorobenzoyl chloride, ethyl chloroformate, methanesulfonyl chloride and p-toluenesulfonyl chloride.

If the molecule contains more than one amino and/or imino group, selective substitution may be possible by suitable protection followed by deprotection as previously described.

A3(e) Conversion of a nitro group into an amino group and optional conversion of an amino group into a mono- or dialkylamino group Conversion of a nitro group into an amino group may be carried out by treating the compound of formula (Ia) (before or after one or more other optional reactions of step A3) with a reducing agent or by catalytic hydrogenation.

Suitable reducing agents include: a combination of an organic carboxylic acid (such as acetic acid or propionic acid) with a metal (such as zinc, iron, nickel or tin); and combinations of stannous chloride with a dilute mineral acid (such as dilute hydrochloric acid or dilute sulfuric acid). Of these, we prefer zinc/acetic acid or stannous chloride/dilute hydrochloric acid. This reaction is preferably effected in the presence of a solvent, the nature of which is not critical, provided that it has no adverse effect upon (although it may participate in) the reaction. Suitable solvents include: water; alcohols, such as methanol or ethanol; aqueous alcohols, such as aqueous methanol or aqueous ethanol; organic carboxylic acids, such as those mentioned above as part of the reducing agent system; and aqueous organic carboxylic acids, again such as those forming part of the reducing agent system.

In the case of catalytic hydrogenation, preferred catalysts include, for example, platinum oxide, palladium black, palladium-on-activated carbon and Raney nickel. Palladium-on-activated carbon is preferably used. The reaction is preferably effected under a hydrogen atmosphere, for example at a hydrogen pressure of from 1 to 10 atmospheres (about 1 to 10 bars). The reaction is preferably effected in the presence of a solvent, the nature of which is not critical, provided that it has no adverse effect on the reaction. Suitable solvents include, for example: alcohols, such as methanol or ethanol; ethers, such as tetrahydrofuran or dioxane; organic carboxylic acids, such as acetic acid or propionic acid; and mixtures of one or more of these organic solvents with water.

The reaction will take place over a wide range of temperatures, but we generally find it convenient to carry out the reaction at a temperature within the range from 0° to 50° C. The time required for the reaction will vary, depending upon many factors, notably the reaction temperature and the nature of the reagents, but a period of from 30 minutes to 2 hours will normally suffice.

Conversion of a free amino group into a mono- or dialkylamino group may be effected by reacting the corresponding amino compound with an alkyl halide (preferably a chloride, bromide or iodide), the nature of the alkyl group depending upon which alkyl group it is desired to introduce. The reaction is preferably effected in the presence of a base. Examples of suitable bases which may be employed include carbonates and bicarbonates, such as sodium carbonate, potassium carbonate, sodium bicarbonate or potassium bicarbonate. The reaction is preferably effected in the presence of an inert solvent, the nature of which is not critical, provided that it has no adverse effect upon the reaction. Suitable solvents include, for example: amides, such as dimethylformamide or dimethylacetamide; sulfoxides, such as dimethyl sulfoxide; alcohols, such as methanol or ethanol; water; and mixtures of one or more of these organic solvents with water.

The reaction will take place over a wide range of temperatures, but we generally find it convenient to carry out the reaction at a temperature of from 0° C. to 100° C. The time required for the reaction will vary, depending upon many factors, but a period of from 30 minutes to 5 hours will normally suffice.

In this reaction, the product will normally be a mixture of the monoalkylamino compound and the dialkylamino compound; use of approximately equimolar amounts of the alkyl halide and of the amino compound will result in the predominant production of the monoalkylamino compound; on the other hand, use of an excess of the alkyl halide will normally favour predominant production of the dialkylamino compound.

A3(f) Conversion of a terminal hydrazino group into a pyrrolyl group

Conversion of a terminal amino group in a hydrazino group into pyrrolyl group can be achieved by reacting the hydrazino compound with a 1,4-diketone compound having the general formula (VII):

$$R^8-CO-(CH_2)_2CO-R^8 \qquad (VII)$$

(in which $R^8$ represents a hydrogen atom or a $C_1$–$C_6$ alkyl group) in an inert solvent.

There is no particular restriction on the nature of the solvent to be employed, provided that it does not interfere with the reaction and that it can dissolve the starting materials at least to some extent. Examples of preferred solvents include: organic carboxylic acids, such as acetic acid or propionic acid; amides, such as dimethylformamide or dimethylacetamide; and alcohols, such as methanol or ethanol. Of these, we prefer the organic carboxylic acids.

The reaction will take place over a wide range of temperatures and the precise temperature chosen is not particulary critical. We generally find it convenient to conduct the reaction at a temperature from 50° C. to 100° C. The time required for the reaction may vary widely, depending on many factors, notably the reaction temperature and the nature of the starting materials employed, but a period of from 1 hour to 5 hours will normally suffice.

A3(g) N-Oxidation, S-oxidation or S,S-dioxidation

The N-oxidation, S-oxidation and/or S,S-dioxidation reactions can be conducted by conventional means, preferably using a peracid, such as perbenzoic acid, or a peroxide, such as hydrogen peroxide, in an inert solvent.

A3(h) Ester hydrolysis

Ester hydrolysis may be carried out by conventional means. For example, the compound may be hydrolyzed by reaction with an alkali metal hydroxide, such as sodium hydroxide or potassium hydroxide, in an inert solvent such as aqueous ethanol, at 0° C. to 100° C. for 10 minutes to 2 hours.

A3(i) Conversion of a carboxy group to an ester group

Conversion of a carboxylic acid compound to the corresponding ester may be accomplished by reaction of the carboxylic acid compound with a corresponding alcohol or by other conventional means. For example, the corresponding carboxylic acid compound may be reacted with a lower diazoalkane, such as diazomethane, diazoethane or diazopropane, at about room temperature in an inert solvent such as diethyl ether.

A3(j) Salification

Salification may be effected by conventional means simply by contacting the base with the chosen acid.

After completion of any of the above reactions, the desired compound can be isolated from the reaction mixture by conventional means. Thereafter, if required, the product can be purified by such conventional techniques as recrystallization or the various chromatography techniques, notably preparative thin layer chromatography or column chromatography.

Method B:

Compounds of the invention can also be prepared as illustrated by the following reaction scheme:

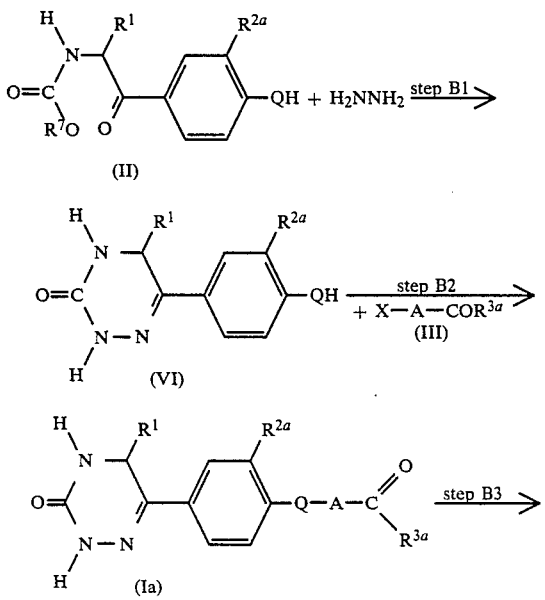

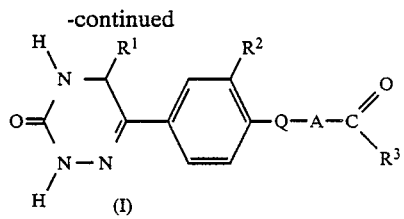

In the above formulae $R^1$, $R^2$, $R^{2a}$, $R^3$, $R^{3a}$, $R^7$, Q and X are as defined above.

The first step, step B1, of this reaction scheme comprises reacting a compound of formula (II) with hydrazine. This is essentially the same as the reaction described in step A2, and may be carried out using the same reagents and reaction conditions.

In step B2, the resulting compound of formula (VI) is then reacted with a haloalkanoic acid or derivative thereof of formula (III). The reaction with the haloalkanoic acid or derivative thereof is essentially the same as the reaction described in step A1, and may be carried out using the same reagents and reaction conditions.

The resulting compound of formula (Ia) may be the desired final product, or it may be subjected to the next step, step B3.

In step B3, where $R^{3a}$ represents a hydroxy group or an ester residue, the compound of formula (Ia) may be reacted with an amine compound of formula H-$R^{3b}$ and/or subjected to any one or more of the other optional reactions, e.g. deprotecting and/or protecting reactions, described in relation to step A3.

After completion of the reaction, the resulting compound of formula (I) may be recovered from the reaction mixture by conventional means. For example, one suitable recovery technique comprises: distilling the solvent from the reaction mixture; mixing the residue with ice-water; extracting the mixture with a water-immiscible organic solvent; washing with water and then drying the extract; and finally distilling the solvent from the extract to give the desired product. If desired, this may be further purified by conventional techniques, for example recrystallization or the various chromatography techniques, particularly column chromatography.

Certain of the compounds of formula (II), used as starting materials are known. Others may be prepared by reacting a compound of general formula (VIII):

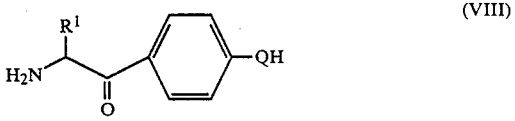

(in which $R^1$ and Q are as defined above), which themselves are known or easily prepared according to a known method [e.g. M. Asscher, Rec. trav. Chim., 68, 960 (1949)] with a chloroformate followed by hydrolyzing the product thus obtained under mild condition.

As can be seen from the results given hereafter in the Test Example, the compounds of the invention potentiated the contractions of the heart significantly better than the known compounds, including amrinone, which is sold commercially for this specific purpose; moreover, the effect of the compounds of the invention was more durable. The compounds have excellent cardiotonic activity, antihypertensive activity, the ability to inhibit gastric secretions and the ability to inhibit blood platelet aggregation.

The compounds of the invention can be administered as conventional pharmaceutical formulations, depending upon the intended route of administration. For example, for oral administration, they may be formulated as powders, granules, tablets, capsules or similar orally administerable formulations, which can be produced by mixing the active compound with carriers, excipients or diluting agents, such as glucose, sucrose, lactose, sorbitol, starch, polyvinylpyrrolidone, mannitol, calcium carbonate, calcium phosphate, sodium chloride or boric acid. For parenteral administration, they may be formulated as conventional injections suitable for, for example, intravenous injection. The dose will vary, depending upon the nature of the disorder, the route of administration, and the symptoms, age and body weight of the patient; however, for an adult human patient, a suitable dose would be from 0.001 mg to 50 mg per day, which could be given in a single dose or in divided doses.

The invention is further illustrated by the following Examples, which illustrate the preparation of various of the compounds of the invention. The preparation of certain of the starting materials employed in these Examples is illustrated in the subsequent Preparations. The activity of certain of the compounds of the invention is illustrated by the subsequent Test Example.

EXAMPLE 1

α-[2-Chloro-4-(2,3,4,5-tetrahydro-5-methyl-3-oxo-1,2,4-triazin-6-yl)phenoxy]-N-[2-(3,4-dimethoxyphenyl)ethyl]acetamide

1(a) Ethyl N-[2-(3-chloro-4-ethoxycarbonyloxyphenyl)-1-methyl-2-oxoethyl]carbamate A suspension of 10.00 g of 1-aminoethyl 3-chloro-4-methoxyphenyl ketone hydrochloride in 60 ml of 47% w/v aqueous hydrobromic acid was heated under reflux for 3.5 hours. At the end of this time, the reaction mixture was concentrated by evaporation under reduced pressure, and then 80 ml of chloroform were added. The mixture was then stirred, whilst ice-cooling, for 5 minutes. At the end of this time, 39 ml of triethylamine were added, and then a solution of 11.4 ml of ethyl chloroformate in 20 ml of chloroform was added dropwise to the suspension over a period of 25 minutes, and the mixture was stirred for 1 hour, whilst ice-cooling. At the end of this time, the mixture was concentrated by evaporation under reduced pressure and then mixed with water and ethyl acetate. The ethyl acetate layer was separated and dried, and then the ethyl acetate used as the solvent was distilled off under reduced pressure. The residue was purified by column chromatography through silica gel eluted with a 9:1 by volume mixture of methylene chloride and diisopropyl ether, to give 10.87 g of the title compound as a brown oil.

1(b) Ethyl N-[2-(3-chloro-4-hydroxyphenyl)-1-methyl-2-oxoethyl]carbamate

A solution of 12.50 g of 85% potassium hydroxide (i.e. potassium hydroxide of purity about 85%, of which the main impurity is water) dissolved in a mixture of 20 ml of water and 30 ml of methanol was added dropwise, whilst ice-cooling, to a solution of 10.87 g of ethyl N-[2-(3-chloro-4-ethoxycarbonyloxyphenyl)-1-methyl-2-oxoethyl]carbamate [prepared as described in step (a) above] in 130 ml of methanol over a period of 5 minutes. The mixture was then stirred at room temperature for 20 minutes. At the end of this time, the mixture was concentrated by evaporation under reduced pressure and then acidified with 5% w/v aqueous hydrochloric acid. It was then extracted with ethyl acetate. The extract was washed with a saturated aqueous solution of sodium chloride and dried. The ethyl acetate of the solvent was then removed by evaporation under reduced pressure. The residue was recrystallized from a mixture of ethyl acetate and hexane, to give 6.12 g of the title compound as a yellowish-brown powder melting at 106°–108° C.

Elemental analysis: Calculated for $C_{12}H_{14}ClNO_4$: C, 53.05%; H, 5.19%; N, 5.16%; Cl, 13.05%. Found: C, 53.17%; H, 5.19%; N, 5.06%; Cl, 13.10%.

1(c) N-[2-(3,4-Dimethoxyphenyl)ethyl]-α-{2-chloro-4-[2-(ethoxycarbonylamino)propionyl]phenoxy}acetamide 505 mg of ethyl N-[2-(3-chloro-4-hydroxyphenyl)-1-methyl-2-oxoethyl]carbamate [prepared as described in step (b) above] were added to a suspension of 81 mg of sodium hydride (as a 55% w/w suspension in mineral oil) in 6 ml of anhydrous dimethylformamide, whilst ice-cooling. The mixture was then stirred at room temperature for 1 hour. The suspension was then cooled, and 476 mg of α-chloro-N-[2-(3,4-dimethoxyphenyl)ethyl]acetamide (prepared as described in Preparation 1) were added thereto. The mixture was stirred at room temperature for 2 hours and then at 100° C. (bath temperature) for 3 hours. At the end of this time, the dimethylformamide used as the solvent was removed by evaporation under reduced pressure, and water was added to the residue. The aqueous mixture was extracted with ethyl acetate, and the extract was washed with a saturated aqueous solution of sodium chloride, dried and concentrated by evaporation under reduced pressure. The residue was purified by column chromatography through silica gel. After elution of impurities with a 2:1 by volume mixture of ethyl acetate and hexane, 556 mg of the title compound were obtained from the fractions eluted with ethyl acetate as a pale yellow powder melting at 113°–114° C.

Elemental analysis: Calculated for $C_{24}H_{29}ClN_2O_7$: C, 58.48%; H, 5.93%; N, 5.68%; Cl, 7.19%. Found: C, 58.71%; H, 5.94%; N, 5.55%; Cl, 7.00%.

1(d) α-[2-Chloro-4-(2,3,4,5-tetrahydro-5-methyl-3-oxo-1,2,4-triazin-6-yl)phenoxy]-N-[2-(3,4-dimethoxyphenyl)ethyl]acetamide A mixture of 556 mg of N-[2-(3,4-dimethoxyphenyl)ethyl]-α-{2-chloro-4-[2-(ethoxycarbonylamino)propionyl]phenoxy}acetamide [prepared as described in step (c) above] and 723 mg of hydrazine hydrate in 7 ml of butanol was heated under reflux for 67 hours. At the end of this time, the mixture was cooled, and the butanol used as the solvent was removed by evaporation under reduced pressure. The residue was purified by column chromatography through silica gel eluted with a 10:1 by volume mixture of chloroform and methanol, to give 112 mg of the title compound as a white powder melting at 167°–169° C. (with decomposition).

Elemental analysis: Calculated for $C_{22}H_{25}ClN_4O_5$, $\frac{3}{8}H_2O$: C, 55.87%; H, 5.61%; N, 11.85%; Cl, 7.50%, Found: C, 55.76%; H, 5.41%; N, 11.70%; Cl, 7.74%.

EXAMPLE 2

α-[2-Chloro-4-(2,3,4,5-tetrahydro-5-methyl-3-oxo-1,2,4-triazin-6-yl)phenoxy]-N-[2-(3,4-dimethoxyphenyl)ethyl]acetamide

2(a)

6-(3-Chloro-4-hydroxyphenyl)-4,5-dihydro-5-methyl-1,2,4-triazin-3(2H)-one 32.64 g of ethyl N-[2-(3-chloro-4-hydroxyphenyl)-1-methyl-2-oxoethyl]carbamate [prepared as described in Example 1(b)] and 75.20 g of 80% hydrazine hydrate (i.e. a grade of hydrazine hydrate containing 20% w/w water) were added to 240 ml of butanol, and the mixture was heated under reflux for 18 hours. The butanol used as the solvent was distilled off under reduced pressure, and then 10% w/v aqueous hydrochloric acid was added, and the mixture was extracted with ethyl acetate. The ethyl acetate layer was washed with a saturated aqueous solution of sodium chloride, dried and concentrated by evaporation under reduced pressure. The residue was collected by filtration, washed with ethyl acetate and dried, to give 14.71 g of the title compound as a yellow powder melting at 218°–222° C. (with decomposition). The filtrate was purified by column chromatography through silica gel eluted with a 10:1 by volume mixture of chloroform and methanol, to give a further 5.64 g of the title compound as a pale yellow powder.

Elemental analysis: Calculated for $C_{10}H_{10}ClN_3O_2$: C, 50.12%; H, 4.21%; N, 17.53%; Cl, 14.79%. Found: C, 50.25%; H, 4.55%; N, 17.33%; Cl, 14.46%.

2(b)

α-[2-Chloro-4-(2,3,4,5-tetrahydro-5-methyl-3-oxo-1,2,4-triazin-6-yl)phenoxy]-N-[2-(3,4-dimethoxyphenyl)ethyl]acetamide 442 mg of 6-(3-chloro-4-hydroxyphenyl)-4,5-dihydro-5-methyl-1,2,4-triazin-3(2H)-one [prepared as described in step (a) above] were added to a stirred suspension of 85 mg of sodium hydride (as a 55% w/w dispersion in mineral oil) in 7 ml of anhydrous dimethylformamide, whilst ice-cooling, and the mixture was stirred at room temperature for 1 hour. To the ice-cooled suspension were then added 472 mg of α-chloro-N-[2-(3,4-dimethoxyphenyl)ethyl]acetamide (prepared as described in Preparation 1), and the reaction mixture was stirred at room temperature for 1 hour and then at 100° C. (bath temperature) for a further 1 hour. The dimethylformamide used as the solvent was removed by evaporation under reduced pressure, and then the mixture was diluted with ethyl acetate. It was then washed with water and with a saturated aqueous solution of sodium chloride, dried and concentrated by evaporation under reduced pressure. The residue was collected by filtration and then recrystallized from a mixture of chloroform and ethyl acetate, to give 326 mg of the title compound as a white powder melting at 167°–169° C. (with decomposition).

EXAMPLES 3 & 4

Following a similar procedure to that described in Example 2(b), the compounds of Examples 3 and 4 were also prepared from 6-(3-chloro-4-hydroxyphenyl)-4,5-dihydro-5-methyl-1,2,4-triazin-3(2H)-one [prepared as described in Example 2(a)] and either, for Example 3, α-chloro-N-propylacetamide (prepared as described in Preparation 3) or, for Example 4, α-chloro-N-phenethylacetamide (prepared as described in Preparation 2):

α-[2-Chloro-4-(2,3,4,5-tetrahydro-5-methyl-3-oxo-1,2,4-triazin-6-yl)phenoxy]-N-propylacetamide (Example 3), melting at 186°–189° C. (with decomposition).

α-[2-Chloro-4-(2,3,4,5-tetrahydro-5-methyl-3-oxo-1,2,4-triazin-6-yl)phenoxy]-N-phenethylacetamide (Example 4), melting at 202°–206° C. (with decomposition).

EXAMPLE 5

Ethyl α-[2-chloro-4-(2,3,4,5-tetrahydro-5-methyl-3-oxo-1,2,4-triazin-6-yl)phenoxy]acetate 2.00 g of 6-(3-chloro-4-hydroxyphenyl)-4,5-dihydro-5-methyl-1,2,4-triazin-3(2H)-one [prepared as described in Example 2(a)] were added, whilst ice-cooling, to a stirred suspension of 364 mg of sodium hydride (as a 55% w/w dispersion in mineral oil) in 30 ml of anhydrous dimethylformamide. The mixture was then stirred at room temperature for 30 minutes, after which 0.89 ml of ethyl chloroacetate was added, and the mixture was stirred at 105°–110° C. (bath temperature) for 1.5 hours. The dimethylformamide used as the solvent was removed by evaporation under reduced pressure, and water and ethyl acetate were added to the resulting residue. The crystals which precipitated were collected by filtration, washed with ethyl acetate and dried to give the title compound as a pale yellowish-brown powder melting at 187°–189° C. (with decomposition). The ethyl acetate layer of the filtrate was separated, washed with a saturated aqueous solution of sodium chloride, dried and concentrated by evaporation under reduced pressure to give crystals, which were collected by filtration, washed with ethyl acetate and dried to give more of the title compound. The total yield was 2.11 g.

Elemental analysis: Calculated for $C_{14}H_{16}ClN_3O_4$: C, 51.62%; H, 4.95%; N, 12.90%; Cl, 10.88%. Found: C, 51.39%; H, 4.88%; N, 12.63%; Cl, 11.07%.

EXAMPLE 6

6-[3-Chloro-4-(2-morpholinoethyl)carbamoylmethoxyphenyl]-5-methyl-4,5-dihydro-1,2,4-triazin-3(2H)-one A mixure of 507 mg of ethyl α-[2-chloro-4-(2,3,4,5-tetrahydro-5-methyl-3-oxo-1,2,4-triazin-6-yl)phenoxy]acetate (prepared as described in Example 5) and 407 mg of N-(2-aminoethyl)morpholine was stirred at 110°–115° C. (bath temperature) for 1 hour. The mixture was cooled and poured into water. The crystals which precipitated were collected by filtration. These crude crystals were recrystallized from a mixture of methanol and ethyl acetate to give 255 mg of the title compound as a white powder melting at 179°–181° C. (with decomposition). The filtrate was extracted with ethyl acetate, dried and concentrated by evaporation under reduced pressure, followed by trituration of the residue with ethyl acetate to give a further 91 mg of the title compound as crystals.

Elemental analysis: Calculated for $C_{18}H_{24}ClN_5O_4$: C, 52.75%; H, 5.90%; N, 17.09%; Cl 8.65%. Found: C, 52.63%; H, 5.87%; N, 16.97%; Cl 8.72%.

EXAMPLE 7

2-[2-Chloro-4-(2,3,4,5-tetrahydro-5-methyl-3-oxo-1,2,4-triazinon-6-yl)phenoxy]-N-ethoxyethylacetamide The title compound, melting at 160°–162° C., was prepared by a procedure similar to that described in Example 6.

EXAMPLE 8

N-(1-Benzyl-4-piperidyl)-α-[2-chloro-4-(2,3,4,5-tetrahydro-5-methyl-3-oxo-1,2,4-triazin-6-yl)phenoxy]acetamide 0.5 g (1.53 mmole) of ethyl α-[2-chloro-4-(2,3,4,5-tetrahydro-5-methyl-3-oxo-1,2,4-triazin-6-yl)phenoxy]acetate (prepared as described in Example 5) was mixed with 0.58 g (3.06 mmole) of 4-amino-1-benzylpiperidine, and the mixture was stirred at 120°–130° C. for 2.5 hours. The mixture was then cooled, after which it was subjected to column chromatography through silica gel and eluted with methylene chloride containing 2% v/v ethanol to give 0.5 g of a pale yellow oil. Trituration of this oil with ethanol yielded crystals, which were then recrystallized from ethanol, to give 0.33 g of the title compound as pale yellow fine crystals melting at 190°–191° C.

EXAMPLE 9

α-[2-Chloro-4-(2,3,4,5-tetrahydro-5-methyl-3-oxo-1,2,4-triazin-6-yl)phenoxy]-N-isobutylacetamide The title compound, melting at 205°–206° C. was prepared by a similar procedure to that described in Example 8.

EXAMPLE 10

α-[2-Chloro-4-(2,3,4,5-tetrahydro-5-methyl-3-oxo-1,2,4-triazin-6-yl)phenoxy-N-[2-(1-piperazinyl)ethyl]acetamide 4.0 g of ethyl α-[2-chloro-4-(2,3,4,5-tetrahydro-5-methyl-3-oxo-1,2,4-triazin-6-yl)phenoxy]acetate (prepared as described in Example 5) and 1.59 g of N-(2-aminoethyl)piperazine were added to 50 ml of ethanol, and the mixture was heated under reflux for 60 hours. The mixture was then cooled, after which the crystals which precipitated were collected by filtration and then recrystallized from ethanol to give 3.44 g of the title compound as pale yellow prisms melting at 208°–210° C.

Elemental analysis: Calculated for $C_{18}H_{25}ClN_6O_3$: C, 52.87%; H, 6.16%; N, 20.55%; Cl, 8.67%. Found: C, 52.77%; H, 6.34%; H, 20.25%; Cl, 8.53%.

EXAMPLE 11

α-[2-Chloro-4-(2,3,4,5-tetrahydro-5-methyl-3-oxo-1,2,4-triazin-6-yl)phenoxy]-N-{2-[4-(p-chlorobenzoyl)-1-piperazinyl]ethyl}acetamide 0.43 g of p-chlorobenzoyl chloride and 0.25 g of triethylamine were added to a suspension of 0.5 g of α-[2-chloro-4-(2,3,4,5-tetrahydro-5-methyl-3-oxo-1,2,4-triazin-6-yl)phenoxy-N-[2-(1-piperazinyl)ethyl]acetamide (prepared as described in Example 10) in 10 ml of tetrahydrofuran, and the mixture was stirred at room temperature for 1 hour. The tetrahydrofuran used as the solvent was removed by evaporation under reduced pressure, and the residue was extracted with methylene chloride. The extract was washed with water and dried over anhydrous magnesium sulfate, after which the residue was purified by column chromatography through silica gel, eluted with a 98:2 by volume mixture of methylene chloride and ethanol, to give 0.2 g of a colorless oil. This oil was crystallized from ethanol and then recrystallized, also from ethanol, to give 0.16 g of the title compound as colorless fine crystals melting at 186°–188° C.

Elemental analysis: Calculated for $C_{25}H_{28}Cl_2N_6O_4$: C, 54.85%; H, 5.16%; N, 15.35%; Cl, 12.95%. Found: C, 54.51%; H, 5.10%; N, 15.30%; Cl, 12.83%.

EXAMPLE 12

α-[2-Chloro-4-(2,3,4,5-tetrahydro-5-methyl-3oxo-1,2,4-triazin-6-yl)phenoxy]-N-{2-[4-(methanesulfonyl)1-piperazinyl]ethyl}acetamide The title compound, melting at 236°–238° C. was prepared by a similar procedure to that described in Example 11.

EXAMPLE 13

α-[2-Chloro-4-(2,3,4,5-tetrahydro-5-methyl-3-oxo-1,2,4-triazin-6-yl)phenoxy]acetohydrazide A solution of 1.0 g of ethyl α-[2-chloro-4-(2,3,4,5-tetrahydro-5-methyl-3-oxo-1,2,4-triazin-6-yl)phenoxy]acetate (prepared as described in Example 5) and 0.39 g of 80% hydrazine hydrate in 10 ml of ethanol was stirred on an oil bath kept at 105° C. for 4 hours. The mixture was then cooled, after which the crystals which precipitated were collected by filtration and recrystallized from ethanol, to give 0.73 g of the title compound as white crystals melting at 252°–254° C.

Elemental analysis: Calculated for $C_{12}H_{14}ClN_5O_3$: C, 46.24%; H, 4.53%; N, 22.47%; Cl, 11.37%. Found: C, 46.24%; H, 4.40%; N, 22.34%; Cl, 11.32%.

EXAMPLE 14

α-[2-Chloro-4-(2,3,4,5-tetrahydro-5-methyl-3-oxo-1,2,4-triazin-6-yl)phenoxy]-N-(2,5-dimethyl-1-pyrrolyl)acetamide 0.27 g of acetonylacetone was added to a solution of 0.5 g of α-[2-chloro-4-(2,3,4,5-tetrahydro-5-methyl-3-oxo-1,2,4-triazin-6-yl)phenoxy]acetohydrazide (prepared as described in Example 13) dissolved in 5 ml of acetic acid, and the mixture was heated at 70° C. for 4 hours. The acetic acid used as the solvent was removed by evaporation under reduced pressure, and the residue was mixed with water to precipitate crystals. These crystals were collected by filtration, washed with water and dried. The product was purified by column chromatography through silica gel (eluent: a 98:2 by volume mixture of methylene chloride and ethanol), followed by recrystallization from ethanol to give 0.4 g of the title compound melting at 189°–190° C.

Elemental analysis: Calculated for $C_{18}H_{20}ClN_5O_3$: C, 55.46%; H, 5.17%; N, 17.96%; Cl, 9.09%. Found: C, 55.45%; H, 5.32%; N, 17.71%; Cl, 8.98%.

EXAMPLE 15

N-(2-Piperidinoethyl)-α-[4-2,3,4,5-tetrahydro-3-oxo-1,2,4-triazin-6-yl)phenoxy]acetamide

15(a)

4,5-Dihydro-6-(p-hydroxyphenyl)-1,2,4-triazin-3-(2H)-one

A mixture of 20 g of ethyl N-(p-hydroxyphenacyl)-carbamate (prepared as described in Preparation 6), 56 g of 80% hydrazine hydrate and 100 ml of butanol was heated under reflux for 30 hours, whilst stirring. The reaction mixture was then concentrated by evaporation under reduced pressure, and the residue was washed with ethanol to give 9.25 g of the title compound as crystals, melting at 266°–269° C. (with decomposition).

15(b) Ethyl α-[4-(2,3,4,5-tetrahydro-3-oxo-1,2,4-triazin-6-yl)phenoxy]acetate 2.74 g of sodium hydride (as a 55% w/w dispersion in mineral oil) were added to a solution of 8 g of 4,5-dihydro-6-(p-hydroxyphenyl)-1,2,4-triazin-3)2H)-one [prepared as described in step (a) above]dissolved in 100 ml of dimethylformamide, and the mixture was stirred at room temperature for 30 minutes. 7.7 g of ethyl chloroacetate were added to the mixture, which was then stirred at 100° to 110° C. for 6 hours. At the end of this time, the reaction mixture was poured into ice-water. The crystals which precipitated were collected by filtration and washed with water and diethyl ether, to afford 7.6 g of the title compound as crystals melting at 181°–183° C.

Infrared Absorption Spectrum (KBr) $v_{max}$cm$^{-1}$: 1690 and 1760.

15(c) Ethyl α-[4-(2,3,4,5-tetrahydro-3-oxo-1,2,4-triazin-6-yl)phenoxy]acetate 0.48 g of sodium hydride )as a 55% w/w dispersion in mineral oil) were added to a solution of 2.23 g of ethyl N-(p-hydroxyphenacyl)carbamate (prepared as described in Preparation 6) dissolved in 50 ml of dimethylformamide. The mixture was stirred at room temperature for 30 minutes, after which 1.35 g of ethyl chloroacetate was added, and the mixture was stirred at 100° to 120° C. for 6 hours. The reaction mixture was then poured into ice-water and extracted with methylene chloride. The organic layer was washed with water, dried over anhydrous magnesium sulfate and concentrated by evaporation under reduced pressure. 50 ml of butanol and 0.62 g of 80% hydrazine hydrate were added to the residue, and the mixture was heated under reflux for 100 hours, whilst stirring. At the end of this time, the reaction mixture was concentrated by evaporation under reduced pressure, and the residue was washed with diethyl ether to give 0.5 g of the title compound having the same properties as the product of step (b) above.

15(d) N-(2-Piperidinoethyl)-α-[4-(2,3,4,5-tetrahydro-3-oxo-1,2,4-triazin-6-yl)phenoxy]acetamide A mixture of 0.416 g of ethyl α-[4-(2,3,4,5-tetrahydro-3-oxo-1,2,4-triazin-6-yl)phenoxy] acetate [prepared as described in step (b) or (c) above]and 0.40 g of 2-piperidinoethylamine was heated at 120° C. for 30 minutes. The reaction mixture was then washed with diethyl ether, and, on recrystallization from ethanol, 0.466 g of the title compound was obtained as colorless scaly crystals melting at 203°–204° C.

EXAMPLE 16

N-[2-(4-Methyl-1-piperazinyl)ethyl]-α-{2-[4-(2,3,4,5-tetrahydro-3-oxo-1,2,4-triazin-6-yl)phenoxy]}acetamide Following the same procedure as described in Example 15(d), the title compound, melting at 203°–204° C., was prepared from ethyl 2-[4-(2,3,4,5-tetrahydro-3-oxo-1,2,4-triazin-6-yl)phenoxy]acetate [prepared as described in Example 15(b) or (c) above] and 2-(4-methyl-1-piperazinyl)ethylamine.

EXAMPLE 17

N-[2-(4-Ethoxycarbonyl-1-piperazinyl)ethyl]-α-[4-(2,3,4,5-tetrahydro-3-oxo-1,2,4-triazin-6-yl)phenoxy]acetamide hemihydrate

17(a) N-[2-(1-Piperazinyl)ethyl]-α-[4-(2,3,4,5-tetrahydro-3-oxo-1,2,4-triazin-6-yl)phenoxy]acetamide hemihydrate A solution of 3.05 g of ethyl α-[4-(2,3,4,5-tetrahydro-3-oxo-1,2,4-triazin-6-yl)phenoxy]acetate [prepared as described in Example 15(b) or (c) above] and 2.13 g of 2-(1-piperazinyl)ethylamine dissolved in 50 ml of ethanol was heated under reflux for 24 hours, whilst stirring. At the end of this time, the crystals which precipitated were collected by filtration and recrystallized from ethanol, to give 3 g of the title compound as colorless fine crystals melting at 177°–180° C.

Mass spectrum, (m/e): 360 (M+).

17(b) N-[2-(4-Ethoxycarbonyl-1-piperazinyl)ethyl]-α-[4-(2,3,4,5-tetrahydro-3-oxo-1,2,4-triazin-6-yl)phenoxy]acetamide hemihydrate 0.15 ml of ethyl chloroformate were added, whilst ice-cooling, to a mixture of 0.360 g of N-[2-(1-piperazinyl)ethyl]-α-[4-(2,3,4,5-tetrahydro-3-oxo-1,2,4-triazin-6-yl)phenoxy]acetamide [prepared as described in step (a) above], 0.13 g of sodium bicarbonate, 10 ml of water and 50 ml of tetrahydrofuran, and the mixture was stirred for 30 minutes. The reaction mixture was then concentrated by evaporation under reduced pressure, and the residue was purified by column chromatography through silica gel (eluent: a 1:1 by volume mixture of ethanol and methylene chloride), followed by recrystallization from ethanol, to give 0.264 g of the title compound as colorless fine crystals melting at 200°–240° C. (with decomposition).

EXAMPLE 18

Ethyl α-[4-(2,3,4,5-tetrahydro-5-methyl-3-oxo-1,2,4-triazin-6-yl)phenoxy]acetate

18(a) 4,5-Dihydro-5-methyl-6-)p-hydroxyphenyl)-1,2,4-triazin-3(2H)-one 1.7 g of ethyl N-(p-hydroxy-α-methylphenacyl)carbamate (prepared as described in Preparation 8) and 4.5 g of 80% hydrazine hydrate were added to 20 ml of butanol, and the mixture was heated under reflux for 56 hours. The butanol was distilled off under reduced pressure, and then the residue was diluted with water. The crystals which precipitated were collected by filtration and washed with water to give the crude title compound as a pale brown powder. This was recrystallized from ethanol to give 0.83 g of the title compound as pale brown prisms, melting at 256°–258° C.

18(b) Ethyl α-[4-(2,3,4,5-tetrahydro-5-methyl-3-oxo-1,2,4-triazin-6-yl)phenoxy]acetate 0.12 g of sodium hydride (as a 55% w/w dispersion in mineral oil) was added to a solution of 0.55 g of 4,5-dihydro-5-methyl-6-(p-hydroxyphenyl)-1,2,4-triazin- 3(2H)-one [prepared as described in step (a) above] dissolved in 6 ml of dimethylformamide, whilst ice-cooling and stirring, and the mixture was stirred at room temperature for 30 minutes. At the end of this time, 0.33 g of ethyl chloroacetate was added. The mixture was then heated at 105° to 110° C. for 3 hours, whilst stirring. The dimethylformamide was then distilled off under reduced pressure, and the residue was diluted with water, after which the mixture was extracted with methylene chloride. The extract was dried over anhydrous magnesium sulfate, and then subjected to column chromatography through silica gel eluted with a 1:50 by volume mixture of ethanol and methylene chloride to give a brown oil. This oil was triturated with ethyl acetate to give crystals, which were recrystallized from ethyl acetate, to give 0.43 g of the title compound as pale yellow needles melting at 152°–153° C.

EXAMPLE 19

N-(2-Morpholinoethyl)-α-[4-(2,3,4,5-tetrahydro-5-methyl-3-oxo-1,2,4triazin-6-yl)phenoxy]acetamide 0.4 g of ethyl α-[4-(2,3,4,5-tetrahydro-5-methyl-3-oxo-1,2,4-triazin-6-yl)phenoxy]acetate (prepared as described in Example 18) was mixed with 0.36 g of 2-morpholinoethylamine, and the mixture was stirred at 115° to 120° C. for 1 hour. The mixture was then cooled, and ethyl acetate was added. The crystals which precipitated were collected by filtration and washed with ethyl acetate to give a pale yellow powder. Recrystallization of this powder from ethyl acetate gave 0.36 g of the title compound as pale brown, fine crystals melting at 147°–149° C.

EXAMPLE 20

N-(2-Morpholinoethyl)-α-[4-(2,3,4,5-tetrahydro-3-oxo-1,2,4-triazin-6-yl)-phenoxy]acetamide

20(a) Ethyl N-[p-[(2-morpholinoethyl)aminocarbonylmethoxy]-phenacyl]carbamate 31 mg of sodium hydride (as a 55% w/w dispersion in mineral oil) were added to a solution of 156 mg of ethyl N-(p-hydroxyphenacyl)carbamate (prepared as described in Preparation 6) dissolved in 10 ml of dimethylformamide. The mixture was then stirred at room temperature for 30 minute, after which 200 mg of 2-chloro-N-(2-morpholinoethyl)acetamide were added, and the mixture was stirred at 100° to 110° C. for 4 hours. The reaction mixture was then poured into ice-water and extracted with methylene chloride. The organic layer was washed with water, dried over anhydrous magnesium sulfate and concentrated by evaporation under reduced pressure. The residue was purified by column chromatography through silica gel eluted with ethyl acetate, to give 190 mg of the title compound as pale yellow needles melting at 133°–135° C.

20(b) N-(2-Morpholinoethyl)-α-[4-(2,3,4,5-tetrahydro3-oxo-1,2,4-triazin-6-yl)phenoxy]acetamide A mixture of 3.93 g of ethyl N-[p-(2-morpholinoethyl)aminocarbonylmethoxy)phenacyl]carbamate [prepared as described in step (a) above], 0.62 g of 80% hydrazine hydrate and 50 ml of butanol was heated under reflux for 100 hours whilst stirring. The reaction mixture was then concentrated by evaporation under reduced pressure, after which the residue was washed with ethanol and recrystallized from ethanol, to give 0.5 g of the title compound as pale brown fine crystals melting at 216°–217° C.

Infrared Absorption Spectrum (KBr) $\nu_{max}$cm$^{-1}$: 1670 and 1705.

Mass spectrum (m/e): 361 (M+).

EXAMPLE 21

Ethyl (2S)-2-{α-[4-2,3,4,5-tetrahydro-3-oxo-1,2,4-triazin-6-yl)phenoxy]acetamido}-3-phenylpropionate

21(a) α-[4-(2,3,4,5-Tetrahydro-3-oxo-1,2,4-triazin-6-yl)phenoxy]acetic acid 2 g (7.21 mmole) of ethyl α-[4-(2,3,4,5-tetrahydro-3-oxo-1,2,4-triazin-6-yl)]phenoxyacetate [prepared as described in Example 15(b)] were mixed with a solution of 0.6 g of potassium hydroxide in 50 ml of water and 40 ml of ethanol. The mixture was then stirred at room temperature for 2 hours, after which it was adjusted to a pH value of 1 by the addition of concentrated hydrochloric acid. The crystals which precipitated were collected by filtration and then recrystallized from a mixture of ethanol and water, to give 1.4 of the title compound as crystals melting at 264°–266° C.

21(b) Ethyl (2S)-3-phenyl-2-{α-[4-(2,3,4,5-tetrahydro-3-oxo-1,2,4-triazin-6-yl)phenoxy]acetamido}-propionate 435 mg of diethyl cyanophosphonate were added to a mixture of 499 mg of α-[4-(2,3,4,5-tetrahydro-3-oxo-1,2,4-triazin-6-yl)phenoxy]acetic acid [prepared as described in step (a) above], 551 mg of ethyl phenylalanate hydrochloride, 0.62 ml of triethylamine and 10 ml of dimethylformamide, whilst ice-cooling, and the mixture was stirred at room temperature for 1 hour. The reaction mixture was then poured into ice-water, after which the crystals which precipitated were collected by filtration and then washed with water. Recrystallization from ethanol gave 672 mg of the title compound as colorless crystals melting at 148°–150° C.

EXAMPLE 22

Ethyl (2S)-2-{α-[2-chloro-4-(2,3,4,5-tetrahydro-3-oxo-1,2,4-triazin-6-yl)phenoxy]acetamido}-3-phenylpropionate A similar procedure to that described in Example 15(a), 15(b), 21(a) and 21(b) was carried out, in that sequence, but using ethyl N-(m-chloro-p-hydroxyphenacyl)carbamate in place of ethyl N-(p-hydroxyphenacyl)carbamate to give the title compound as crystals melting at 180°–181° C.

EXAMPLE 23

Ethyl (2S)-2-{α-[2-methyl-4-(2,3,4,5-tetrahydro-3-oxo-1,2,4-triazin-6-yl)phenoxy]acetamido}-3-phenylpropionate A similar procedure to that described in Examples 15(a), 15(b), 21(a) and 21(b) was carried out, in that sequence, but using ethyl N-(p-hydroxy-m-methylphenacyl)carbamate in place of ethyl N-(p-hydroxyphenacyl)carbamate to give the title compound as white crystals, melting at 148°–150° C.

EXAMPLE 24

Ethyl (2S)-3-(3-pyridyl)-2-{α-[4-(2,3,4,5-tetrahydro-3-oxo-1,2,4-triazin-6-yl)phenoxy]acetamido}-propionate A similar procedure to that described in Example 21(b) was carried out, but using methyl (3-pyridyl)alanate in place of ethyl phenylalanate to give the title compound as crystals melting at 132°–135° C. (with decomposition).

PREPARATION 1

α-Chloro-N-[2-(3,4-dimethoxyphenyl)ethyl]acetamide 4.5 ml of triethylamine were added to a solution of 5.11 g of 2-(3,4-dimethoxyphenyl)ethylamine dissolved in 35 ml of methylene chloride, and the mixture was stirred, whilst ice-cooling. 2.4 ml of chloroacetyl chloride were then added dropwise to the mixture over a period of 5 minutes, after which the mixture was stirred for 15 minutes, whilst ice-cooling. The reaction mixture was then concentrated by evaporation under reduced pressure, and ethyl acetate was added to the resulting residue. The ethyl acetate solution was washed, in turn, with water, with a 5% w/v aqueous solution of sodium bicarbonate, with 10% w/v aqueous hydrochloric acid and with a saturated aqueous solution of sodium chloride. It was then dried, and the solvent was distilled off under reduced pressure. The residue was recrystallized from a mixture of ethyl acetate and hexane, to give 5.77 g of the title compound as pale yellow-brown, featherlike crystals melting at 92–94° C.

PREPARATION 2

α-Chloro-N-phenethylacetamide 5 ml of triethylamine were added to a solution of 3.64 g of phenethylamine dissolved in 35 ml of methylene chloride, and the mixture was stirred, whilst ice-cooling. 2.63 ml of chloroacetyl chloride were then added dropwise to the mixture over a period of 5 minutes, after which it was stirred for 30 minutes whilst ice-cooling. The reaction mixture was then concentrated by evaporation under reduced pressure, after which ethyl acetate was added to the residue. The ethyl acetate solution was washed, in turn, with water, with a 5% w/v aqueous solution of sodium bicarbonate, with 10% w/v aqueous hydrochloric acid and with a saturated aqueous solution of sodium chloride. It was then dried, and the solvent was distilled off. The residue was recrystallized from a mixture of ethyl acetate and hexane, to give 4.96 g of the title compound as pale yellow-brown needles melting at 62°–65° C.

PREPARATION 3

α-Chloro-N-propylacetamide 35 ml of triethylamine were added to a solution of 1.24 g of propylamine dissolved in 25 ml of methylene chloride, and the mixture was stirred for minutes, whilst ice-cooling. At the end of this time, 1.84 ml of chloroacetyl chloride was added dropwise over a period of 5 minutes, and then the mixture was stirred for 30 minutes, whilst ice-cooling. The reaction mixture was then concentrated by evaporation under reduced pressure, after which ethyl acetate was added to the residue. The resulting ethyl acetate solution was washed with water, with a 5% w/v aqueous solution of sodium bicarbonate, with 10% w/v aqueous hydrochloric acid and with a saturated aqueous solution of sodium chloride, after which it was dried. The extract was then concentrated by evaporation under reduced pressure, to give 1.81 g of the title compound as a red oil.

PREPARATION 4

α-Amino-p-methoxyacetophenone hydrochloride 45.82 g of α-bromo-p-methoxyacetophenone were dissolved in 400 ml of methylene chloride, and 28.04 g of hexamethylenetetramine were added to the solution, which was then stirred at room temperature for 2 hours. The crystals which precipitated were collected by filtration. 200 ml of ethanol and 100 ml of concentrated hydrochloric acid were added to these crystals, and the mixture was stirred at room temperature for 18 hours. The reaction mixture was then concentrated by evaporation under reduced pressure, and the residue was dissolved in water. The aqueous solution was made alkaline by the addition of a 20% w/v aqueous solution of potassium carbonate and was then extracted with ethyl acetate. The ethyl acetate extract was washed with a saturated aqueous solution of sodium chloride and dried over anhydrous magnesium sulfate. A 4N solution of hydrochloric acid in dioxane was then added. The crystals which precipitated were collected by filtration, to give to 30.7 g of the title compound as yellow fine crystals melting at 201° C. (with decomposition).

PREPARATION 5

Ethyl p-(α-ethoxycarbonylamino)acetylphenylcarbonate

A mixture of 30.7 g of a α-amino-p-methoxyacetophenone hydrochloride (prepared as described in Preparation 4) and 150 ml of 47% w/v aqueous hydrobromic acid was heated under reflux for 5 hours, whilst stirring. The reaction mixture was then concentrated by evaporation under reduced pressure, and the residue was dissolved in 500 ml of methylene chloride and 63.6 ml of triethylamine. 28.9 ml of ethyl chlorocarbonate were added dropwise to the solution, whilst ice-cooling, and the mixture was stirred for 1 hour. The reaction mixture was then washed with water, dried over anhydrous magnesium sulfate and concentrated by evaporation under reduced pressure. The residue was washed with diisopropyl ether, to give 25.04 g of the title compound as crystals melting at 84°–87° C.

Infrared Absorption Spectrum (KBr) $\nu_{max}$cm$^{-1}$: 1680, 1715 and 1750.

PREPARATION 6

Ethyl N-(p-hydroxyphenacyl)carbamate

A mixture of 25 g of ethyl p-(α-ethoxycarbonylamino)acetylphenylcarbonate (prepared as described in Preparation 5), 7.13 g of potassium hydroxide, 40 ml of water and 160 ml of methanol was stirred at room temperature for 2 hours. At the end of this time, the reaction mixture was poured into ice-water and neutralized with concentrated hydrochloric acid. The crystals which precipitated were collected by filtration and washed with water, to give 17.85 g of the title compound as crystals melting at 137°–140° C.

Infrared Absorption Spectrum (KBr) $\nu_{max}$cm$^{-1}$: 1670 and 1690.

PREPARATION 7

Ethyl p-(α-ethoxycarbonylamino)propionylphenylcarbonate 165 ml of 47% w/v aqueous hydrobromic acid were added to 16.5g of α-amino-4-methoxypropiophenone, and the mixture was heated under reflux for 3 hours. At the end of this time, the mixture was freed from hydrobromic acid by evaporation under reduced pressure, to give a reddish brown oil. 160 ml of methylene chloride were added to this oil, and then 54.2 g of triethylamine and 19.1 g of ethyl chlorocarbonate were added to the resulting solution, whilst ice-cooling, after which the mixture was stirred for 1.5 hours. Ice-water was then added to the mixture and the methylene chloride solution was washed with water. The solution was then dried over anhydrous magnesium sulfate. The methylene chloride was then distilled off under reduced pressure, and the residue was subjected to column chromatography through silica gel eluted with methylene chloride containing 1% v/v ethanol. 6.4 g of the title compound were obtained as a reddish brown oil.

Infrared Absorption Spectrum (liquid film) $\nu_{max}$cm$^{-1}$: 1690, 1715 and 1765.

PREPARATION 8

Ethyl N-(p-hydroxy-α-methylphenacyl)carbamate 6.4 g of ethyl p-(α-ethoxycarbonylamino)propionylphenylcarbonate (prepared as described in Preparation 7) were added to 70 ml of methanol. A solution of 6.97 g of 85% potassium hydroxide in a mixture of 60 ml of methanol and 10 ml of water was then added to the resulting solution, whilst ice-cooling, and the mixture was stirred at the same temperature for 5 minutes and then at room temperature for 30 minutes. The methanol was then distilled off under reduced pressure, and the residue was adjusted to a pH value of 7 by adding water and 6N aqueous hydrochloric acid. The mixture was then extracted with ethyl acetate and dried over anhydrous magnesium sulfate. The ethyl acetate was then removed from the mixture by evaporation under reduced pressure, and the residue was subjected to column chromatography through silica gel eluted with methylene chloride containing 2% v/v ethanol, to give 3.4 g of a brown oil, which was triturated with diisopropyl ether. The precipitated crystals were filtered off and then washed with diisopropyl ether, to give 2.5 g of the title compound as a pale yellow powder. Recrystallization from diisopropyl ether gave the title compound as pale yellow prisms melting at 114°–115° C.

TEST EXAMPLE

Cardiac Activity in the Dog Heart

Following the method reported by Alousi et al [Circulation Research 45, 666 (1979)], a fine catheter, having a pressure transducer built in at the tip, was inserted into the carotid artery of an anaesthetised dog in the direction of the heart. The tip of the catheter was placed in the left ventricle and the pressure waveform obtained was recorded as a linear differential value. The maximum value of this pressure wave was taken as the contractility of the left ventricle.

Each test compound was dissolved in 0.1N hydrochloric acid and administered intravenously, and the percentage increase in contractive power from its level immediately prior to administration, as well as the recovery time (in minutes) are shown in the following Table 2. The recovery time measured was the time taken, after administration of the test compound, for the heart contractive power to return to its level immediately prior to administration.

For purposes of comparison, the following structurally similar compounds were similarly tested:

Compound A=2,3,4,5-tetrahydro-6-(4-hydroxyphenyl)-5-methyl-3-oxo-1,2,4-triazine:

Compound B=2,3,4,5-tetrahydro-6-(4-benzyloxyphenyl)-5-methyl-3-oxo-1,2,4-triazine:

Compound C=N-benzyl-α-[4-(2,3,4,5-tetrahydro-3-oxo-1,2,4-triazin-6-yl)phenoxy]acetamide—this compound is analogous to certain of the compounds disclosed in European Patent Publication No. 52 442;

Compound D=amrinone, whose systematic name is 5-amino-(3,4'-bipyridin)-6(1H)-one, and which is currently used as a cardiotonic agent.

In this test, the cardiotonic effect of amrinone at a dose of 0.3 mg/kg iv was taken as 1, and the relative activity ratios of each drug were calculated, adjusted to correspond to equivalent dosages. These results are also shown in the following Table 2.

TABLE 2

| Cpd No. | Dosage (mg/kg) | Contractive power (% increase) | Recovery time (minutes) | Activity ratio |
| --- | --- | --- | --- | --- |
| 41 | 0.003 | 14 | 38 | 30 |
| 54 | 0.003 | 35 | 65 | 150 |
| 73 | 0.003 | 22 | 74 | 130 |
| 83 | 0.003 | 25 | 17 | 40 |
| 96 | 0.003 | 19 | 56 | 70 |
| 155 | 0.010 | 29 | 40 | 51 |
| 162 | 0.010 | 22 | 34 | 33 |
| 189 | 0.010 | 18 | 31 | 21 |
| 221 | 0.003 | 15 | 49 | 10 |
| 240 | 0.003 | 51 | 31 | 14 |
| A | 0.030 | 25 | 18 | 4 |
| B | 0.100 | 8 | 16 | 0.3 |
| C | 0.030 | 20 | 26 | 5 |
| D | 0.300 | 21 | 27 | 1 |

As can seen from the above results, the compounds of the invention potentiated the contractions of the heart significantly better than the other compounds, including amrinone, which is sold commercially for this specific purpose; moreover, the effect of the compounds of the invention was more durable.

We claim:

1. A compound of formula (I):

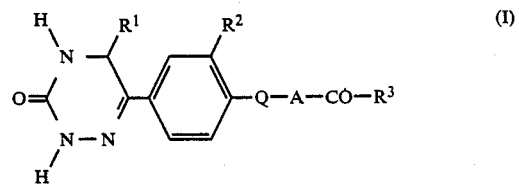

wherein:

R$^1$ represents a hydrogen atom or a C$_1$–C$_6$ alkyl group; R$^2$ represents a hydrogen atom, a halogen atom, a C$_1$–C$_6$ alkyl group, a substituted C$_1$–C$_6$ alkyl group having at least one halogen atom, a nitro group, an amino group, a protected amino group, an alkylamino group in which the alkyl part is C$_1$–C$_6$, a dialkylamino group in which each alkyl part is C$_1$–C$_6$, a cyano group, a carbamoyl group, an alkylcarbamoyl group in which the alkyl part is C$_1$–C$_6$, a dialkylcarbamoyl group in which each alkyl part is $C_1-C_6$, a ureido group, an alkylureido group in which the alkyl part is $C_1-C_6$, a dialkylureido group in which each alkyl part is $C_1-C_6$, a carboxy group or a protected carboxyl group;

Q represents an oxygen atom or a sulfur atom;

A represents a $C_1-C_6$ alkylene group;

$R^3$ represents a hydroxy group, a $C_1-C_6$ alkoxy group, an aryloxy group, an aralkyloxy group in which the alkyl part has from 1 to 6 carbon atoms or a group of formula $-(NH)_n-NR^5R^6$, wherein n is 0 or 1; and $R^5$ and $R^6$ are independently selected from the group consisting of hydrogen atoms; $C_1-C_{10}$ alkyl groups; $C_2-C_6$ alkenyl groups; $C_3-C_7$ cycloalkyl groups; aryl groups; heterocyclic groups, and substituted $C_1-C_{10}$ alkyl groups having at least one substituent selected from the group consisting of substituent (a) defined below; or $R^5$ and $R^6$, together with the nitrogen atom to which they are attached, form a heterocyclic group as defined below;

substituents (a):

halogen atoms, hydroxy groups, $C_1-C_6$ alkoxy groups, aryloxy groups, aralkyloxy groups in which the alkyl part has from 1 to 6 carbon atoms, carboxy groups, protected carboxy groups, carbamoyl groups, alkylcarbamoyl groups in which the alkyl part is $C_1-C_6$ dialkylcarbamoyl groups in which each alkyl part is $C_1-C_6$, $C_3-C_7$ cycloalkyl groups, aryl groups, heterocyclic groups, amino groups, protected amino groups and substituted amino groups having one or two substituents selected from the group consisting of $C_1-C_6$ alkyl groups, aryl groups and heterocyclic groups;

said protected amino group is an amino group protected with a group selected from the group consisting of $C_1-C_7$ aliphatic carboxylic acyl groups; substituted $C_1-C_7$ aliphatic carboxyl acyl groups having at least halogen or $C_1-C_4$ alkoxy groups; arylcarbonyl groups; aralkyloxy carbonyl groups in which the alkyl part is $C_1-C_6$; and aralkyl groups in which the alkyl part is $C_1-C_6$;

said protected carboxy group is a carboxy group protected with a group selected from the group consisting of $C_1-C_6$ alkyl groups, aralkyl groups in which the alkyl part is a $C_1-C_6$ alkyl, $C_2-C_5$ aliphatic acyloxymethyl groups, 1-($C_2-C_7$ alkoxycarbonyloxy)ethyl groups, phthalidyl group (2-oxo-5-methyl-1,3-dioxolen-4-yl)methyl group, (2-oxo-5-phenyl-1,3-dioxolen-4-yl)methyl group, $C_1-C_6$ alkoxymethyl groups and halogenated $C_1-C_6$ alkyl groups;

said aryl groups and aryl parts of groups containing an aryl are phenyl or naphthyl groups which are unsubstituted or have at least one substituent selected from the group consisting of halogen atoms, hydroxy group, $C_1-C_6$ alkoxy groups, $C_1-C_6$ alkyl groups, halogenated $C_1-C_6$ alkyl groups, nitro groups, sulfamoyl groups and $C_1-C_6$ alkylsulfamoyl groups;

said heterocyclic groups and heterocyclic parts of groups containing a heterocyclic group are groups selected from the group consisting of tetrahydrofuryl, tetrahydropyranyl, tetrahydrothienyl, tetrahydrothiopyranyl, aziridinyl, azetidinyl, pyrrolidinyl, piperidyl, hexahydroazepinyl, imidazolidinyl, oxazolidinyl, thiazolidinyl, morpholinyl, thiomorpholinyl, piperazinyl, homopiperazinyl, furyl, thienyl, pyrrolyl, pyridyl, oxazolyl, thiazolyl and pyrimidinyl groups which are unsubstituted or have at least one substituent selected from the group consisting of substituent (b):

substituent (b): phenyl groups; naphthyl groups; substituted phenyl or naphthyl groups having at least one substituent selected from the group consisting of halogen atoms, $C_1-C_4$ ethyl groups, $C_1-C_4$ alkoxy groups and trifluoromethyl groups; $C_1-C_4$ alkyl groups; substituted $C_1-C_4$ alkyl groups having at least one substituent selected from the group consisting of hydroxyl groups, phenyl groups and substituted phenyl groups having at least one substituent selected from the group consisting of halogen atoms, $C_1-C_4$ alkyl groups, $C_1-C_4$ alkoxy groups and trifluoromethyl groups; $C_1-C_7$ alkanoyl groups; substituted $C_2-C_7$ alkanoyl groups having at least one substituent selected from the group consisting of furyl groups, thienyl groups, pyridyl groups, $C_3-C_7$ cycloalkyl groups, halogen atoms, $C_1-C_4$ alkoxy groups and phenyl groups; $C_2-C_5$ Alkoxycarbonyl groups; aralkyloxycarbonyl groups wherein the alkyl part is $C_1-C_4$ and the aryl part is phenyl or naphthyl groups or substituted phenyl or naphthyl groups having at least one substituent selected from the group consisting of halogen, $C_1-C_4$ alkyl, $C_1-C_4$ alkoxy and trifluoromethyl groups; benzoyl groups; naphthoyl groups; substituted benzoyl or naphthoyl groups having at least one substituent selected from the group consisting of halogen atoms, sulfamoyl groups, $C_1-C_4$ alkyl groups and $C_1-C_4$ alkoxy groups; furyl carbonyl groups; thienyl carbonyl groups; pyridylcarbonyl groups; $C_1-C_4$ alkylsulfonyl groups; arylsulfonyl groups, wherein the aryl part is phenyl or naphthyl groups, or substituted phenyl or naphthyl groups having at least one substituent selected from the group consisting of halogen atoms, $C_1-C_4$ alkyl groups, $C_1-C_4$ alkoxy groups and trifluoromethyl groups; the carbamoyl group; mono- and di- alkylcarbamoyl groups wherein the alkyl part is $C_1-C_4$; furyl groups; thienyl groups; pyridyl groups and oxygen atoms;

or a pharmaceutically acceptable acid addition salt thereof; and providing that:

when $R^2$ represents said hydrogen atom or said nitro, amino or cyano group, then $R^3$ represents a group of formula $-(NH)_n-NHR^6$, where n is 0 or 1 and $R^6$ represents said $C_1-C_6$ alkyl group having at least one heterocyclic substituent.

2. A compound as claimed in claim 1, in which:

$R^1$ represents a hydrogen atom or a $C_1-C_4$ alkyl group;

$R^2$ represents a halogen atom or a $C_1-C_6$ alkyl group;

Q represents an oxygen atom or a sulfur atom;

A represents a $C_1-C_4$ alkylene group;

$R^3$ represents a group of formula $-(NH)_n-NR^5R^6$, wherein n is 0 or 1; and $R^5$ and $R^6$ are independently selected from the group consisting of hydrogen atoms, $C_1-C_6$ alkyl groups, $C_2-C_6$ alkenyl groups and substituted $C_2-C_4$ alkyl groups having at least one substituent selected from the group consisting of substituents (a''); and substituents (a''): $C_1-C_6$ alkoxy groups, $C_3-C_7$ cycloalkyl groups, aryl groups and said heterocyclic groups;

or a pharmaceutically acceptable acid addition salt thereof.

3. A compound as claimed in claim 1, in which:
$R^1$ represents a hydrogen atom or a methyl group;
$R^2$ represents a halogen atom or a methyl group;
Q represents an oxygen atom;
A represents a $C_1$-$C_4$ alkylene group;
$R^3$ represents a group of formula —$NHR^6$, wherein
$R^6$ represents a $C_1$-$C_6$ alkyl group, a substituted $C_2$-$C_4$ alkyl group having at least one substituent selected from the group consisting of substituents (a''') or a $C_2$-$C_6$ alkenyl group;
substituents (a'''): $C_1$-$C_4$ alkoxy groups, $C_5$ or $C_6$ cycloalkyl groups, phenyl groups, substituted phenyl groups having at least one substituent selected from the group consisting of substituents (b') and said heterocyclic groups having 5 or 6 ring atoms; and
substituents (b'): $C_1$-$C_4$ alkyl groups, halogen atoms, the trifluoromethyl group and $C_1$-$C_4$ alkoxy groups;
or a pharmaceutically acceptable acid addition salt thereof.

4. A compound as claimed in claim 1, which is selected from the group consisting of α-[2-chloro-4-(2,3,4,5-tetrahydro-5-methyl-3-oxo-1,2,4-triazin-6-yl)phenoxy]-N-isobutylacetamide or a pharmaceutically acceptable salt thereof.

5. A compound as claimed in claim 1, which is selected from the group consisting of α-[2-chloro-4-(2,3,4,5-tetrahydro-5-methyl-3-oxo-1,2,4-triazin-6-yl)-phenoxy]-N-propylacetamide or a pharmaceutically acceptable salt thereof.

6. A compound as claimed in claim 1, which is selected from the group consisting of α-[2-chloro-4-(2,3,4,5-tetrahydro-5-methyl-3-oxo-1,2,4-triazin-6-yl)phenoxy]-N-(2-ethoxyethyl)acetamide or a pharmaceutically acceptable salt thereof.

7. A compound as claimed in claim 1, which is selected from the group consisting of α-[2-chloro-4-(2,3,4,5-tetrahydro-5-methyl-3-oxo-1,2,4-triazin-6-yl)phenoxy]-N-(3-ethoxypropyl)acetamide or a pharmaceutically acceptable salt thereof, 8. A compound as claimed in claim 1, which is selected from the group consisting of α-[2-chloro-4-(2,3,4,5-tetrahydro-3-oxo-1,2,4-triazin-6-yl)phenoxy]-N-phenethylacetamide or a pharmaceutically acceptable salt thereof.

9. A compound as claimed in claim 1, which is selected from the group consisting of α-[2-chloro-4-(2,3,4,5-tetrahydro-5-methyl-3-oxo-1,2,4-triazin-6-yl)phenoxy]-N-phenethylacetamide or a pharmaceutically acceptable salt thereof.

10. A compound as claimed in claim 1, which is selected from the group consisting of α-[2-chloro-4-(2,3,4,5-tetrahydro-5-methyl-3-oxo-1,2,4-triazin-6-yl)phenoxy]-N-[2-(3,4-dimethoxyphenyl)ethyl]acetamide or a pharmaceutically acceptable salt thereof.

11. A compound as claimed in claim 1, which is selected from the group consisting of α-[2-chloro-4-(2,3,4,5-tetrahydro-3-oxo-1,2,4-triazin-6-yl)phenoxy]-N-(2-morpholinoethyl)acetamide or a pharmaceutically acceptable salt thereof.

12. A compound as claimed in claim 1, which is selected from the group consisting of α-[2-chloro-4-(2,3,4,5-tetrahydro-5-methyl-3-oxo-1,2,4-triazin-6-yl)phenoxy]-N-(2-morpholinoethyl)acetamide or a pharmaceutically acceptable salt thereof.

13. A compound as claimed in claim 1, which is selected from the group consisting of α-[2-chloro-4-(2,3,4,5-tetrahydro-5-methyl-3-oxo-1,2,4-triazin-6-yl)phenoxy]-N-{2-[4-(4-chlorobenzoyl)-1-piperazinyl]ethyl}acetamide or a pharmaceutically acceptable salt thereof.

14. A compound as claimed in claim 1, which is selected from the group consisting of α-[2-chloro-4-(2,3,4,5-tetrahydro-5-methyl-3-oxo-1,2,4-triazin-6-yl)phenoxy]-N-[2-(4-methanesulfonyl-1-piperazinyl)ethyl]acetamide or a pharmaceutically acceptable salt thereof.

15. A compound as claimed in claim 1, which is selected from the group consisting of α-[2-chloro-4-(2,3,4,5-tetrahydro-5-methyl-3-oxo-1,2,4-triazin-6-yl)phenoxy]-N-(1-benzyl-4-piperidyl)acetamide and pharmaceutically acceptable salts thereof.

16. A pharmaceutical composition for the treatment of cardiac disorders comprising a cardiotonically effective amount of the compound of claim 1 in a pharmaceutically acceptable carrier, diluent or excipient.

17. A pharmaceutical composition as claimed in claim 16, in which:
$R^1$ represents a hydrogen atom or a $C_1$-$C_4$ alkyl group;
$R^2$ represents a halogen atom or a $C_1$-$C_6$ alkyl group;
Q represents an oxygen atom or a sulfur atom;
A represents a $C_1$-$C_4$ alkylene group;
$R^3$ represents a group of formula —$(NH)_n$—$NR^5R^6$, wherein
n is 0 or 1; and
$R^5$ and $R^6$ are independently selected from the group consisting of hydrogen atoms, $C_1$-$C_6$ alkyl groups, $C_2$-$C_6$ alkenyl groups and substituted $C_2$-$C_4$ alkyl groups having at least one substituent selected from the group consisting of substituents (a''); and
substituents (a''): $C_1$-$C_6$ alkoxy groups, $C_3$-$C_7$ cycloalkyl groups, aryl groups and heterocyclic groups;
or a pharmaceutically acceptable acid addition salt thereof.

18. A pharmaceutical composition as claimed in claim 16, in which;
$R^1$ represents a hydrogen atom or a methyl group;
$R^2$ represents a halogen atom or a methyl group;
Q represents an oxygen atom;
A represents a $C_1$-$C_4$ alkylene group;
$R^3$ represents a group of formula —$NHR^6$, wherein
$R^6$ represents a $C_1$-$C_6$ alkyl group, a substituted $C_2$-$C_4$ alkyl group having at least one substituent selected from the group consisting of substituents (a''') or a $C_2$-$C_6$ alkenyl group;
substituents (a'''): $C_1$-$C_4$ alkoxy groups, $C_5$ or $C_6$ cycloalkyl groups, phenyl groups, substituted phenyl groups having at least one substituent selected from the group consisting of substituents (b') and heterocyclic groups having 5 or 6 ring atoms; and
substituents (b'): $C_1$-$C_4$ alkyl groups, halogen atoms, the trifluoromethyl group and $C_1$-$C_4$ alkoxy groups;
or a pharmaceutically acceptable acid addition salt thereof.

19. A pharmaceutical composition as claimed in claim 16, wherein said cardiotonic agent is selected from the group consisting of:

α-[2-chloro-4-(2,3,4,5-tetrahydro-5-methyl-3-oxo-1,2,4-triazin-6-yl)phenoxy]-N-isobutylacetamide;

α-[2-chloro-4-(2,3,4,5-tetrahydro-5-methyl-3-oxo-1,2,4-triazin-6-yl)phenoxy]-N-propylacetamide;

α-[2-chloro-4-(2,3,4,5-tetrahydro-5-methyl-3-oxo-1,2,4-triazin-6-yl)phenoxy]-N-(2-ethoxyethyl)acetamide;

α-[2-chloro-4-(2,3,4,5-tetrahydro-5-methyl-3-oxo-1,2,4-triazin-6-yl)phenoxy]-N-(3-ethoxypropyl)acetamide;

α-[2-chloro-4-(2,3,4,5-tetrahydro-3-oxo-1,2,4-triazin-6-yl)phenoxy]-N-phenethylacetamide;

α-[2-chloro-4-(2,3,4,5-tetrahydro-5-methyl-3-oxo-1,2,4-triazin-6-yl)phenoxy]-N-phenethylacetamide;

α-[2-chloro-4-(2,3,4,5-tetrahydro-5-methyl-3-oxo-1,2,4-triazin-6-yl)phenoxy]-N-[2-(3,4-dimethoxyphenyl)ethyl]acetamide;

α-[2-chloro-4-(2,3,4,5-tetrahydro-3-oxo-1,2,4-triazin-6-yl)phenoxy]-N-(2-morpholinoethyl)acetamide;

α-[2-chloro-4-(2,3,4,5-tetrahydro-5-methyl-3-oxo-1,2,4-triazin-6-yl)phenoxy]-N-(2-morpholinoethyl)acetamide; α-[2-chloro-4-(2,3,4,5-tetrahydro-5-methyl-3-oxo-1,2,4-triazin-6-yl)phenoxy]-N-{2-[(4-(4-chlorobenzoyl)1-piperazinyl]ethyl}acetamide;

α-[2-chloro-4-(2,3,4,5-tetrahydro-5-methyl-3-oxo-1,2,4-triazin-6-yl)phenoxy]-N-[2-(4-methanesulfonyl-1-piperazinyl)ethyl]acetamide;

α-[2-chloro-4-(2,3,4,5-tetrahydro-5-methyl-3-oxo-1,2,4-triazin-6-yl)phenoxy]-N-(1-benzyl-4-piperidyl)acetamide;

or a pharmaceutically acceptable salt thereof.

20. A method of treating cardiac disorders in an animal comprising administering to said animal, a cardiotonically effective amount of the compound of claim 1.

21. A method as claimed in claim 20, in which:
$R^1$ represents a hydrogen atom or a $C_1$-$C_4$ alkyl group;
$R^2$ represents a halogen atom or a $C_1$-$C_6$ alkyl group;
Q represents an oxygen atom or a sulfur atom;
A represents a $C_1$-$C_4$ alkylene group;
$R^3$ represents a group of formula —$(NH)_n$—$NR^5R^6$, wherein
n is 0 or 1; and
$R^5$ and $R^6$ are independently selected from the group consisting of hydrogen atoms, $C_1$-$C_6$ alkyl groups, $C_2$-$C_6$ alkenyl groups and substituted $C_2$-$C_4$ alkyl groups having at least one substituent selected from the group consisting of substituents (a''); and
substituents (a''): $C_1$-$C_6$ alkoxy groups, $C_3$-$C_7$ cycloalkyl groups, aryl groups and heterocyclic groups;
or a pharmaceutically acceptable acid addition salt thereof.

22. A method as claimed in claim 20, in which:
$R^1$ represents a hydrogen atom or a methyl group;
$R^2$ represents a halogen atom or a methyl group;
Q represents an oxygen atom;
A represents a $C_1$-$C_4$ alkylene group;
$R^3$ represents a group of formula —$NHR^6$, wherein
$R^6$ represents a $C_1$-$C_6$ alkyl group, a substituted $C_2$-$C_4$ alkyl group having at least one substituent selected from the group consisting of substituents (a''') or a $C_2$-$C_6$ alkenyl group;
substituents (a'''): $C_1$-$C_4$ alkoxy groups, $C_5$ or $C_6$ cycloalkyl groups, phenyl groups, substituted phenyl groups having at least one substituent selected from the group consisting of substituents (b') and heterocyclic groups having 5 or 6 ring atoms; and
substituents (b'): $C_1$-$C_4$ alkyl groups, halogen atoms, the trifluoromethyl group and $C_1$-$C_4$ alkoxy groups;
or a pharmaceutically acceptable acid addition salt thereof.

23. A method as claimed in claim 20, wherein said cardiotonic agent is selected from the group consisting of:

α-[2-chloro-4-(2,3,4,5-tetrahydro-5-methyl-3-oxo-1,2,4-triazin-6-yl)phenoxy]-N-isobutylacetamide;

α-[2-chloro-4-(2,3,4,5-tetrahydro-5-methyl-3-oxo-1,2,4-triazin-6-yl)phenoxy]-N-propylacetamide;

α-[2-chloro-4-(2,3,4,5-tetrahydro-5-methyl-3-oxo-1,2,4-triazin-6-yl)phenoxy]-N-(2-ethoxyethyl)acetamide;

α-[2-chloro-4-(2,3,4,5-tetrahydro-5-methyl-3-oxo-1,2,4-triazin-6-yl)phenoxy]-N-(3-ethoxypropyl)acetamide;

α-[2-chloro-4-(2,3,4,5-tetrahydro-3-oxo-1,2,4-triazin-6-yl)phenoxy]-N-phenethylacetamide;

α-[2-chloro-4-(2,3,4,5-tetrahydro-5-methyl-3-oxo-1,2,4-triazin-6-yl)phenoxy]-N-phenethylacetamide;

α-[2-chloro-4-(2,3,4,5-tetrahydro-5-methyl-3-oxo1,2,4-triazin-6-yl)phenoxy]-N-[2-(3,4-dimethoxyphenyl)ethyl]acetamide;

α-[2-chloro-4-(2,3,4,5-tetrahydro-3-oxo-1,2,4triazin-6-yl)phenoxy]-N-(2-morpholinoethyl)acetamide;

α-[2-chloro-4-(2,3,4,5-tetrahydro-5-methyl-3-oxo1,2,4-triazin-6-yl)phenoxy]-N-(2-morpholinoethyl)acetamide;

α-[2-chloro-4-(2,3,4,5-tetrahydro-5-methyl-3-oxo-1,2,4-triazin-6-yl)phenoxy]-N-{2-[4-(4-chlorobenzoyl)1-piperazinyl]ethyl}acetamide;

α-[2-chloro-4-(2,3,4,5-tetrahydro-5-methyl-3-oxo-1,2,4-triazin-6-yl)phenoxy]-N-[2-(4-methanesulfonyl-1-piperazinyl)ethyl]acetamide;

α-[2-chloro-4-(2,3,4,5-tetrahydro-5-methyl-3-oxo 1,2,4-triazin-6-yl)phenoxy]-N-(1-benzyl-4-piperidyl)acetamide;

or a pharmaceutically acceptable salt thereof.

* * * * *